(12) United States Patent
Erickson

(10) Patent No.: US 8,329,980 B2
(45) Date of Patent: *Dec. 11, 2012

(54) TRANSGENIC PRODUCTION IN BOVINE SALIVA

(76) Inventor: Jeffrey P. Erickson, East Woodstock, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/834,534

(22) Filed: Jul. 12, 2010

(65) Prior Publication Data

US 2010/0281549 A1 Nov. 4, 2010

(51) Int. Cl.
*A01K 67/027* (2006.01)
*A01K 67/00* (2006.01)
*C12N 15/00* (2006.01)

(52) U.S. Cl. .............................. 800/15; 800/13; 800/21

(58) Field of Classification Search .................... 800/15, 800/13, 21
See application file for complete search history.

(56) References Cited

U.S. PATENT DOCUMENTS

| | | | | |
|---|---|---|---|---|
| 4,476,777 | A | 10/1984 | Dutchburn | 99/421 H |
| 4,873,191 | A | 10/1989 | Wagner et al. | 435/317.1 |
| 5,175,384 | A | 12/1992 | Krimpenfort et al. | 800/11 |
| 5,445,958 | A | 8/1995 | Feldman | 435/214 |
| 5,476,777 | A | 12/1995 | Holly et al. | 435/214 |
| 5,565,350 | A | 10/1996 | Kmiec | 435/463 |
| 5,641,670 | A | 6/1997 | Treco et al. | 435/325 |
| 5,756,325 | A | 5/1998 | Kmiec | 435/463 |
| 5,811,279 | A | 9/1998 | Kaetsu et al. | 435/214 |
| 6,037,457 | A | 3/2000 | Lord | 530/413 |
| 6,140,552 | A | 10/2000 | Deboer et al. | 800/15 |
| 7,772,459 | B2 * | 8/2010 | Erickson | 800/4 |

FOREIGN PATENT DOCUMENTS

WO WO/91/12650 8/1991
WO WO/93/09222 5/1993

OTHER PUBLICATIONS

Altschul et al., "Basic Local Alignment Research Tool", *J. Mol Biol* 215: 403-410 (1990).
Baum et al., "In vivo gene transfer to salivary glands," *Critical Reviews in Oral Biology & Medicine* 10(3): 276-283 (1999).
Baum et al., "Polarized secretion of transgene products from salivary glands in vivo, " *Human Gene Theraoy*, 10:2789-2797 (1999).
Belitser et al., "Fibrinogen-fibrin interaction," *Biochim. et Biophys Acta* 154: 367-375 (1968).
Binnie et al., "Characterization of purified recombinant fibrinogen: partial phosphorylation of fibrinopeptide A," *Biochemistry* 32: 107-113 (1993).
Boscovic et al., "Studies of the role factor Va in the factor Xa-catalyzed activation of prothrombin, fragment 1-2-prethrombin-2, and dansyl-1-glutamyl-glycyl-1-arginine-meizothrombin in the absence of phospholipids," *J. Biol. Chem.* 265(18): 10497-1010505 (1990).

Degen, "The prothrombin gene and its liver-specific expression," *Seminars in Thrombosis and Hemostasis* 18(2): 230-242 (1992).
Degen et al., "Characterization of the complementary deoxyribonucleic acid and gene coding for human prothrombin," *Biochemistry* 22: 2087-2097 (1983).
Degen et al., "Characterization of the cDNA coding for mouse prothrombin and localization of the gene on mouse chromosome 2," *DNA Cell Biol.* 9: 487-498 (1990).
Dempfle et al., "Purification of human plasma fibrinogen by chromatography on protamine-agarose," *Thromb. Res.* 46:19-27 (1987).
Denman et al., "Transgenic expression of a variant of human tissue-type plasminogen activator in goat milk: purification and characterization of the recombinant enzyme," *Bio/Technology* 9: 839-843 (1991).
Doolittle, R. F., "Searching through sequence databases" *Met Enz* 183: 99-110 (1990).
Ebert et al.,"A Moloney MLV-rat somatotropin fusion gene produces biologically active somatotropin in a transgenic pig," *Mol. Endoc.* 2: 277-283 (1988).
Ebert and DiTullio, "The production of human pharmaceuticals in milk of transgenic animals," pp. 36-41 in The Natural Environment: Interdisciplinary Views: Proceedings (1995).
Ebert and Schindler, "Transgenic Farm Animals: Progress Report," *Theriogenology* 39: 121-135 (1993).
Ebert et al., Transgenic production of a variant of human tissue—type plasminogen activator in goat milk: generation of transgenic goats and analyses of expression, *Bio/Technology* 9: 835-838 (1991).
Ebert et al., "Induction of human tissue plasminogen activators in the mammary gland of transgenic goats," *Bio/Technology* 12: 699-702 (1994).
Fell, L.R.; Shutt, D.A., "Use of salivary cortisol as an indicator of stress due to management practices in sheep and calves" *Proceedings of the Australian Society of Animal Production*, 16: 203-206 (1986).
Franza et al., "Activation of human prothrombin by a procoagulant fraction from the venom of echis carinatus," *J. Biol. Chem.* 250(7): 7057-7068 (1965).
Gunzel and Hoppe, "Eine technik zum anlagen einer oesophagusfistel beim schaf," *DTW-DtschTierarztl-Wochenschr* 83(9): 407-408 (1976).
Hammer et al., "Production of transgenic rabbits, sheep and pigs by microinjection," *Nature* 315:680-682 (1985).
Haverkate et al., "Fibrinogen milano II: a congenital dysfibrinogenaenia associated with juvenile arterial and venous thrombosis," *Thromb. Haemostasis* 55: 131-135 (1986).
Heldebrandt et al.,"The activation of prothrombin: I. Isolation and preliminary characterization of intermediates," *J. Biol. Chem.* 248(10): 3642-3652 (1973).
Holm et al., "Purification and characterization of 3 fibrinogens with different molecular weights obtained from normal human plasma," *Thromb. Res.* 37: 165-176 (1985).

(Continued)

*Primary Examiner* — Gerald Leffers, Jr.
*Assistant Examiner* — Magdalene Sgagias
(74) *Attorney, Agent, or Firm* — Medlen & Carroll, LLP

(57) ABSTRACT

The invention relates to the production of proteins and other substances of interest in saliva of transgenic animals, particularly in mammals that produce large quantities of saliva, particularly monogastric ruminants, and ovine, caprine and bovine mammals. Preferred embodiments of the invention relate in particular to the production of foreign and modified proteins in the transgenic saliva of these animals, including particularly human fibrinogen, human prothrombin and human thrombin, among others. The invention relates as well to methods, devices, genetic constructs and to transgenic constructs for making the proteins and other substances of interest, to novel saliva and saliva-derived compositions, novel products produced from the saliva, and to uses of the saliva, saliva-derived compositions and novel products.

20 Claims, No Drawings

OTHER PUBLICATIONS

Irwin et al.,"Identification of transgenic mice by PCR analysis of saliva," *Nature Biotechnology* 14(9): 1146-1148 (1996).

Koppert et al., "A monoclonal antibody, specific for human fibrinogen, fibrinopeptide a-containing fragments and not reacting with free fibrinopeptide A," *Blood* 66: 503-507 (1985).

Krimpenfort, P. J. A., "Generation of transgenic dairy cattle using 'in vitro' embryo production," *Bio/Technology* 9(9), 844-847 (1991).

Krishnaswamy et al., "The prothrombinase-catalyzed activation of prothrombin proceeds through the intermediate meizothrombin in an ordered, sequential reaction," *J. Biol. Chem.* 261(19): 8977-8984 (1986).

Larson et al., "High-level salivary gland expression in transgenic mice," *Transgenic Research* 3(5): 311-316 (1994).

Lindner et al., "Saliva collection and relationship between lactate concentration in blood and saliva of exercising horses," *J Equine Vet Sci* 20(1): 52-54 (2000).

Lorand, L., "Fibrinoligase: the fibrin-stabilizing factor system of blood plasma," *Ann. N. Y. Acad. Sci.* 202(6), 6-30 (1972).

Lubon et al., "Blood proteins from transgenic animal bioreactors," *Transfusion Medicine Reviews* X(2): 131-143 (1996).

Lutz et al., "Techniques for collecting daliva from awake, unrestrained, adult monkeys for cortisol assay," *Am. Journal of Primatology* 52(2): 93-99 (2000).

MacGillivray et al., "Recombinant genetic approaches to functional mapping of thrombin," *Ann. N.Y. Acad Sci.* 485: 73-79 (1986).

Meyers and Miller: "Optimal alignments in linear space," *Computer Applications in the Biosciences*: 4(1) 11-17 (1988).

Mihalyi, "Physicochemical studies of bovine fibrinogen.IV. ultraviolet absorption and its relation to the structure of the molecule," *Biochemistry* 7: 208-223 (1968).

Mikkelsen et al., "Tissue-specific expression in the salivary glands of transgenic mice," *Nature* 20(9): 2249-2255 (1992).

Miller, "Nonenzymic control of prothrombin activation," *Ann. N.Y. Acad. Sci.* 370 336-342 (1981).

Miller,"The nonenzymic activation of prothrombin by polylysine," *J. Biol. Chem.* 236: 63-64 (1960).

Mirels et al., "Characterization of the rat salivary-gland B1-immunoreactive proteins," *Biochemical Journal* 330 (Part 1): 437-444 (1998).

Needleman and Wunsch: "A general method applicable to the search for similarities in amino acid sequence of two proteins" *J Mol Biol* 48: 443-453 (1970).

Ng et al., "Quantifying thrombin-catalyzed release of fibrinopeptides from fibrinogen using high-performance liquid chromatography,"*Methods Enzymol.* 222: 341-358 (1993).

Ou et al., "Using sodium chloride step gradients to fractionate DNA fragments," *Biotechniques*, 10(4): 446-450 (Apr. 1991).

Palmiter et al., "Transgenic Mice," *Cell* 41: 343-345 (1985).

Phillips et al., "A technique for saliva collection in dogs," *Laboratory Animal Science* 33(5):465-466 (1983).

Poulsen et al., "Coordination of murine parotid secretory protein and salivary amylase expression, " *EMBO J.* 5: 1891-1896 (1986).

Rhee et al., "Role of meizothrombin and meizothromblin-(des Fl) in conversion of prothrombin to thrombin by the echis carinatus venom coagulant," *Biochemistry* 21: 3437-3443 (1982).

Rosing et al., "Formation of meizothrombin as intermsdiate in factor Za-cataalyzed prothrombin activation," *J. Biol. Chem.* 261 (9): 4224-4228 (1986).

Sahlu et al., "Application of $^{13}CO_2$ measurements to the estimation of energy expenditure in goats" *Canadian Journal of Animal Science* 72(2): 245-252 (1992).

Seegers et al.,"Some properties of purified prothrombin and its activation with sodium citrate, "*Blood* 5; 421-433 (1950).

Shaw and Schibler, "Structure and expression of the parotid secretory protein gene of mouse," *J Mol Biol*, 192: 567-576 (1986).

Shiba et al., "Antibody-detectable changes in fibrinogen adsorption affecting platelet activation on polymer surfaces," Amer. J. Physiol. 260:C965-C974 (1991).

Smith and Waterman "Identification of common molecular subsequences," *J Mol Biol*, 147: 195-197 (1981).

Takebe et al., "Calcium ion-dependent monoclonal antibody against human fibrinogen: preparation, characterization, and application to fibrinogen purification," *Thromb Haemost* 73: 662-667 (1995).

Tans et al., "Meizothrombin formation during factor Xa-catalyzed prothrombin activation," *J. Biol. Chem.* 266(32): 21864-2873 (1991).

Tijburg et al., "Formation of meizothrombin as intermediate in factor Xa-catalyzed prothrombin activation on endothelial cells," *J. Biol. Chem.* 266(6): 4017-4022 (1991).

Valenzuela, R. et al., "Immunoelectrophoretic and Immunohistochemical Characterizations of Fibrinogen Derivatives in Atherosclerotic Aortic Intimas and Vascular Prosthesis Pseudointimas," *Am. J. Pathol.*, 141(4), 861-880 (1992).

Walker et al., "The activation of prothrombin by the prothrombinase complex," *J. Biol. Chem.*, 269(44): 27441-227450 (1994).

Wright et al., "High level expression of active human alpha-1-antitrypsin in the milk of transgenic sheep," *Bio/Technology*, 9: 830-834 (1991).

\* cited by examiner

TRANSGENIC PRODUCTION IN BOVINE SALIVA

FIELD OF THE INVENTION

The invention relates to the production of foreign or modified proteins in saliva of transgenically modified animals. In addition, some aspects of the invention relate to animals genetically engineered to produce non-natural components in saliva. In certain further aspects the invention relates to animals genetically engineered to produce non-natural components in their saliva to modify its composition.

BACKGROUND

The hallmark contribution of genetic engineering is technology that, when properly applied, can be used to elucidate precisely and alter in a controlled way—with base by base resolution—the genotype and thereby the phenotypic characteristics of living organisms. Two long-recognized applications of genetic engineering technology that stem from this contribution and promise great humanitarian, scientific and commercial benefits are the creation of improved organisms and the creation of organisms that can be used to produce substances other than those for which they are naturally useful.

As to the first of these goals, genetic engineering has been applied during the past two decades in a wide range of efforts to create improved organisms for food production. To mention just a few, these efforts include endeavors: to produce improved strains and varieties of agricultural plants; to produce livestock that utilize feed more efficiently; to endow livestock with greater resistance to parasites and disease; to create livestock that provides more healthful food; to alter livestock so that it is less harmful to the environment; and to produce plants and animals that benefit the environment. Regarding the production of transgenic farm animals, for instance, see Ebert (1989), *Gene transfer through embryo microinjection*, pgs 233-250 in ANIMAL BIOTECHNOLOGY: COMPREHENSIVE BIOTECHNOLOGY, FIRST SUPPLEMENT, Eds. Babiuk et al., Pergamon Press and, for another review in this regard, also see Ebert and Schindler (1993), *Transgenic Farm Animals: Progress Report, Theriogenology* 39: 121-135.

Towards the second goal, genetic engineering has been applied to the production of a wide variety of substances in plants and animals, most often proteins of pharmaceutical interest. These efforts largely have been directed, in animals, to the production of xeno-substances in the milk of livestock animals—primarily swine, ovine, caprine and bovine animals. Regarding the production of pharmaceuticals in milk see, for instance, Ebert and DiTullio (1995), *The production of human pharmaceuticals in milk of transgenic animals*, pgs 36-41 in THE NATURAL ENVIRONMENT: Interdisciplinary Views: Proceedings. Among efforts to produce substances in this way have been those aimed at the production of hormones, antibodies, enzymes, and factors involved in or related to hemostasis, to name just a few. These endeavors have met with varying degrees of success, as discussed below. Generally, complex polypeptides that undergo extensive post-translational modification have been produced successfully only in animals, and for the most part attempts to produce commercially valuable amounts of these products has been restricted to mammary gland expression and to isolation of proteins from milk.

Although none of these efforts have been entirely successful, several efforts to produce proteins transgenicly in milk have met with some success, and a number of proteins of pharmaceutical interest have been transgenicly expressed in mammary gland cells, and isolated from milk in a biologically active form. For an early review in this regard, see in pertinent part, for instance, Ebert and Schindler (1993), *Transgenic Farm Animals: Progress Report, Theriogenology* 39: 121-135. For instance, tPA has been produced in goat milk (see Ebert et al. (1991), *Transgenic production of a variant of human tissue-type plasminogen activator in goat milk I: Generation of transgenic goats and analyses of expression, Bio/Technology* 9: 835-838). And high levels of active human alpha-1-anti-trypsin have been produced in sheep milk (see Wright et al. (1991), *High level expression of active human alpha-1-anti-trypsin in the milk of transgenic sheep, Bio/Technology* 9: 830-834). Nevertheless, success has not been general and transgenic mammary gland-specific expression has not, as yet, been used to produce a pharmaceutical protein that has entered the marketplace.

Part of the reason for the overall difficulty in bringing these transgenic products to market may lie with disadvantages of present methods for transgenic production in milk. First, efficiency of transgenic production in mammary glands and milk is significantly reduced by gender specificity. Although males can be induced to lactate, they cannot be made to produce milk in quantities useful for commercial production of transgenic substances. See, for instance, Ebert et al. (1994), *Induction of human tissue plasminogen activators in the mammary gland of transgenic goats, Bio/Technology* 12: 699-702, and also Ebert (1988), *A Moloney MLV somatotropin fusion gene produces biologically active somatotropin in a transgenic pig, Mol. Endoc.* 2: 277-283. Practically all of the milk for commercial production of transgenic products using mammary gland-specific expression therefore must come from the females in a transgenic herd. Since, the quantities of milk useful to produce transgenic substances commercially therefore can be obtained only from the female "half" of a herd, milk based transgenic production methods are approximately 50% less efficient in utilizing a herd population than otherwise similarly efficient technology that is gender-neutral. Other aspects of milk-based transgenic production methods may make up for this relative disadvantage over other technologies; but, gender neutrality is nonetheless desirable, and would be an advantage even to milk based production.

Second, although lactation can be induced in immature animals of either sex, and milk thereby can be obtained in quantities sufficient to assess transgenic expression, there is nonetheless a delay from the time transgenic expression is proved in an immature animal to the time the animal can produce milk in quantities useful for commercial production of transgenic substances. In some species, moreover, the volume of milk produced simply is insufficient to support commercial production of proteins, at levels of expression and secretion that can be achieved in mammary gland cells. Even in mammals that produce the necessary volumes of milk, lactation often must be induced and is cyclically variable. Both induction and cyclic variability can be disadvantages of milk based production compared to methods that rely on processes that occur in a continuous manner throughout the life of an animal, without intervention, and without much variation.

In addition, efforts to produce transgenic products in milk have encountered a variety of other problems. Deleterious effects of endogenous milk constituents, such as proteases, on the desired transgenic product, have been observed. Premature shut-down of lactation has occurred in females expressing mammary specific transgenic proteins. In this regard see, for example, Ebert and Schindler (1993), *Transgenic Farm*

*Animals: Progress Report, Theriogenology* 39: 121-135. Transgenic mammary gland expression can have deleterious effects on the health of an animal, either directly as a result of the presence in the animal of the transgenic protein or other substance, or as a consequence of induced hyper-lactation necessary to obtain necessary levels of milk production. Finally, while mammary gland-specific expression and secretion into milk appears to modify and process properly a few proteins, it may not do so for others. Inability of mammary gland cells and milk to carry out post-translational processes thus still may prove to be an impediment to commercial production, even if other obstacles can be avoided or overcome.

Perhaps because of such difficulties, mammary gland-specific transgenic expression of particular proteins in milk has not been as widely used for commercial production of transgenic proteins, as might have been expected from the reports on research scale expression. Several other systems have been considered for transgenic production and efforts have been and are being made to use them to produce proteins and, perhaps, other substances. Thus far, each of these systems has problems and/or disadvantages that have prevented their use for commercial production of transgenic proteins or substances, particularly proteins that are produced initially as inactive pro-enzymes that are subject to complex processes of post-translational proteolytic processing and/or modification. There have been several reports on expression of exogenous genes in salivary glands of transgenic animals, for instance. Baum and co-workers reviewed some work in this regard directed to clinical applications, repair of hypofunctional gland parenchyma, in particular, and the production of secretory transgene products for systemic or upper gastrointestinal tract pharmaceutical use (Baum at al. (1999), *Critical Reviews in Oral Biology & Medicine* 10(3): 276-283. The work described by Baum et al. (1999) related to gene transfer therapy and, apparently, did not aim for commercially advantageous production of proteins, or other substances, in transgenic saliva. Thus, it is relatively uninformative in this regard.

Reports on work directed more specifically to transgenic salivary gland-specific expression have been published by Mikkelsen and co-workers, Larson and co-workers, and Mirels and co-workers (citations follow). Mikkelsen and co-workers reported expression of a Factor VIII-derived polypeptide in saliva of genetically engineered mice. See Mikkelsen et al., (1992), *Nature* 20(9): 2249-2255. Larson and co-workers also reported salivary gland expression of exogenous gene constructs in transgenic mice. See Larson et al. (1994), *Transgenic Research* 3(5): 311-316. Mire's and co-workers characterized the genes for rat salivary-gland B1-immunoreactive proteins of adult (and neonatal) rat sublingual and parotid glands (often referred to as the B1-IPs), that also are the major secretory products of rat submandibular gland acinar-cell progenitors. See Mirels at al. (1998), *Biochemical Journal* 330 (Part 1): 437-444. This work was carried out in species that produce very small quantities of saliva. It is not informative on saliva-specific expression in other mammals, particularly not in ruminants that produce saliva in large volumes. Moreover, apparently only very small amounts of transgenic protein were detected in the saliva, and the work thus is not informative about economically viable and/or commercially advantageous transgenic production of polypeptides and/or proteins and/or other substances in saliva. Apparently, given the lack of further publications, this work has not been pursued, perhaps because of these drawbacks or others.

In sum, present transgenic technologies for pharmaceutical protein production have achieved significant success; but, they have not, as yet, supported commercially advantageous and economically viable production of a marketed pharmaceutical product. Therefore a need exists for improved transgenic animals, methods and technology for commercially advantageous and economically viable production of products for the veterinary and human health care markets, such as pharmaceutical peptides and/or polypeptides and/or proteins, and other substances. Particularly, there is a need for transgenic animals, methods and technology for the commercially advantageous and economically viable production of pharmaceuticals that undergo complex post-translational processing and modification, especially those that cannot be obtained in useful form and quantity by presently available methods of production.

SUMMARY

In light of the foregoing background, it is therefore among the objects of certain aspects and preferred embodiments of the invention herein disclosed to provide animals, methods, compositions, devices, technologies, systems and the like for the commercially advantageous and/or economically viable production of desired substances, particularly polypeptides and/or proteins, in saliva of transgenic animals, particularly non-human mammals that produce large volumes of saliva.

In certain preferred aspects of the invention further in this regard, as discussed more fully below, it is among the objects of certain highly preferred embodiments to provide animals, methods, compositions, devices, technologies, systems and the like for the commercially advantageous and/or economically viable production of certain desired proteins, particularly human blood proteins, especially, human antibodies, human albumins, human vWFs, human fibrinogens, human prothrombins and/or human thrombins, especially human fibrinogen, human prothrombin and/or human thrombin, in the saliva of monogastric ruminant transgenic non-human mammals, particularly porcine, ovine, caprine and/or bovine mammals, especially bovine non-human mammals.

In accordance therewith and with other aspects of the invention, it is an object of the invention in certain aspects to provide in certain of its preferred embodiments animals, methods, compositions, devices, technologies, systems and the like for the commercially advantageous and/or economically viable production of desired polypeptides and/or proteins in and from the saliva of transgenic animals, including single-chain proteins, multi-chain proteins, and polypeptides, including relatively short polypeptides also referred to as peptides and/or oligopeptides.

Especially in the foregoing regards, the invention provides in certain further aspects and preferred embodiments animals, methods, compositions, devices, technologies, systems and the like for the commercially advantageous and/or economically viable production of desired polypeptides and/or proteins in and from the saliva of transgenic animals, including probioactive and/or bioactive polypeptides and/or proteins in single-chain proteins, multi-chain proteins, and polypeptides, including relatively short polypeptides also referred to as peptides and/or oligopeptides.

Also especially in this regard, the invention provides in certain further aspects and particularly preferred embodiments animals, methods, compositions, devices, technologies, systems and the like for the commercially advantageous and/or economically viable production of desired probioactive and/or bioactive pharmaceutical proteins and/or other pharmaceutical polypeptides in and from the saliva of transgenic animals, including probioactive and/or bioactive single-chain pharmaceutical proteins, probioactive and/or bioactive multi-chain pharmaceutical proteins, and probioactive and/or bioactive pharmaceutical polypeptides, including probioactive and/or bioactive peptides (relatively short polypeptides, also referred to as peptides and/or oligopeptides).

In all these regards, in accordance with further of its objects, the invention in certain aspects and further particularly preferred embodiments provides animals, methods, compositions, devices, technologies, systems and the like for the commercially advantageous and/or economically viable transgenic production of desired probioactive and/or bioactive pharmaceutical proteins and/or other pharmaceutical polypeptides in and from the saliva of transgenic animals, including probioactive and/or bioactive single-chain pharmaceutical proteins, probioactive and/or bioactive multi-chain pharmaceutical proteins, and probioactive and/or bioactive pharmaceutical polypeptides, including probioactive and/or bioactive peptides (relatively short polypeptides, also referred to as peptides and/or oligopeptides), wherein the aforementioned polypeptides and/or proteins are (and/or are selected from the group consisting of) phytases, antibodies, growth hormones, and blood proteins including, but not limited to, serum albumin and proteins of hemostasis, especially in this regard fibrinogen, prothrombin, thrombin and von Willebrand Factor ("vWF"), very especially in this regard human serum albumin, human fibrinogen, human prothrombin, human thrombin and human vWF, very especially particularly human fibrinogen, human prothrombin and/or human thrombin.

In accordance with the above, in certain further aspects the invention provides in further particularly preferred embodiments animals, methods, compositions, devices, technologies, systems and the like for the commercially advantageous and/or economically viable transgenic production of desired proteins, polypeptides and/or other substances as described above, wherein the transgenic proteins, polypeptides and/or other substances differ from the non-transgenic, naturally occurring proteins, polypeptides and/or other substances in its structure, particularly in covalent structure and/or in activity, especially covalent structure. In one aspect in this regard, in certain particularly preferred embodiments the transgenic substances are the polypeptides and/or proteins described above (including all of the single-chain proteins, multi-chain proteins, and/or other polypeptides described above, in both probioactive and bioactive forms, including the particularly named groups and species of proteins named above, including but not limited to phytases, growth hormones, antibodies, albumins, vWFs, fibrinogens, prothrombins and thrombins, particularly human vWF, human fibrinogen, human prothrombin and human thrombin, especially human fibrinogen and/or human prothrombin and/or human thrombin), and they differ from their non-transgenic naturally occurring form in one or more structures and/or one or more structural features and/or one or more characteristics produced by post-translational processing and/or one or more post-translational modifications, including but not limited to structural features produced by proteolytic cleavage and/or processing, and post-translational covalent modifications including but not limited to glycosylation, acetylation, gamma-carboxylation, methylation, sulfation, and poly-ADP-ribosylation. In particularly preferred embodiments in this regard, the structural differences do not diminish and preferably increase the effectiveness and/or utility of the product, especially in this regard, the ease of regulatory approval and effectiveness as a medicament and/or therapeutic agent.

In another aspect in these regards, the invention provides in certain of its preferred embodiments transgenic polypeptides and proteins in accordance with the foregoing that differ in their primary amino acid sequence from that of the naturally occurring non-transgenic polypeptide or protein. In further preferred embodiments in this regard the polypeptide and/or protein differs from the non-transgenic, naturally occurring polypeptide and/or protein in primary structure and in structures produced by post-translational processing and/or modification. In yet other preferred embodiments in this regard the transgenic substances have substantially the same or the same activities as the non-transgenic substances, but in other preferred embodiments in this regard the transgenic substances differ from the non-transgenic substances in one or more of their activities and/or their specific activities.

In yet additional aspects in this regard, the invention provides in certain particularly preferred embodiments non-naturally occurring substances produced by a transgenic animal in accordance with the foregoing and as described elsewhere herein, wherein the transgenic polypeptide and/or protein and/or other substance differs from that occurring in nature in its complexation with itself to form multimers or with other substances, and/or it comprises a moiety not present in the polypeptide and/or protein and/or other substance as it occurs in nature, and/or wherein the polypeptide and/or protein or other substance does not comprise a moiety present in the polypeptide and/or protein or other substance as it occurs in nature In yet further aspects in this regard the invention provides in certain particularly preferred embodiments non-naturally occurring substances produced by a transgenic animal in accordance with the foregoing and as described elsewhere herein, wherein the transgenic polypeptide and/or protein differs from that occurring in nature in its primary structure, and wherein its amino acid sequence differs from the amino acid sequence of the polypeptide and/or protein as it occurs in non-transgenic animals but otherwise has 80% to 90%, preferably 90% to 95%, and more preferably 95% to 98%, identity with the amino acid sequence of the polypeptide and/or as it occurs when isolated from its natural host animal. Among preferred embodiments in this regard are those wherein further the polypeptide and/or protein has one or more activities of the polypeptide and/or protein as it occurs naturally, those wherein the polypeptide and/or protein has one or more activities with substantially the same or the same specific activity as the specific activity of the polypeptide and/or protein as it naturally occurs, and those wherein one or more activities are different and/or substantially different in a desired way, either less or more, than those of the polypeptides and/or proteins, as it is occurs naturally. Particularly preferred embodiments in all these regards include those in which one or more of the aforementioned activities is a physiological activity, those in which one or more activities are an enzymatic activity, a binding activity, an intra-cellular transport, those in which one or more activities are physiological persistence and/or half life, and those in which one or more activities are pharmacological activities, particularly pharmacological activities effective for treating disorder or disease in a patient.

In still yet further aspects in this regard, in accordance with the foregoing, the invention provides in certain further particularly preferred embodiments one or more non-naturally occurring polypeptides and/or proteins, wherein the transgenic polypeptide and/or protein differs in its specific activity from that of the naturally occurring polypeptide and/or protein, wherein in certain especially preferred embodiments in this regard, the specific activity, as a percent of that of the purified, natural polypeptide and/or protein, wherein the specific activity in certain especially preferred embodiments in this regard is or is selected from the group consisting of specific activities within the range of 25% to 95%, 50% to 95%, 75% to 95%, 80% to 97%, 85% to 98%, 90% to 105%, 75% to 125%, 50% to 110%, 90% to 110%, about 100%, 100%, and more than 110% of the specific activity of the homogeneously pure, fully active polypeptide and/or protein isolated from its natural source.

In another aspect, the invention provides in certain aspects and preferred embodiments non-naturally occurring saliva that differs in composition from the composition of the naturally occurring saliva of the non-transgenic animal. The invention further provides in certain preferred embodiments in this regard non-naturally occurring saliva comprising substances that differ in the saliva as to kind or amount or both from those that occur naturally in the saliva of the non-transgenic animal, including in particularly preferred embodiments the aforementioned polypeptides and/or proteins. In these and other regards, in preferred embodiments of the invention saliva of the invention differs from the saliva that occurs naturally in the non-transgenic animal, entirely or in part, as a result of expression of a transgene, wherein in certain preferred embodiments in this regard the transgene is expressed specifically in salivary gland cells. In a related aspect, the invention provides in preferred embodiments saliva that differs from non-transgenic naturally occurring saliva of the animal not only in these regards but also in one or more other alterations and/or changes in composition resulting from the action, bio-activity or bio-activities of one or more transgenic peptides and/or polypeptides and/or single chain proteins and/or multi-chain proteins on the synthesis, concentration, degradation, complexation, modification, conformation, distribution, activity, mobility and/or biochemical and/or biological activities and/or specific activities of one or more of naturally occurring saliva constituents, and/or the biophysical or biochemical properties of the saliva.

In another aspect the invention provides transgenic animals that produce non-naturally occurring saliva that differs in its composition from the saliva that occurs naturally in the non-transgenic animal. In yet another related aspect of the invention in this regard, certain of the preferred embodiments provide transgenic animals genetically engineered to express in their saliva a product that does not naturally occur therein. In both of these and other aspects of the invention in certain of the particularly preferred embodiments the saliva contains a transgenic peptide and/or polypeptide and/or single-chain protein and/or multi-chain protein, wherein the transgenic peptide and/or polypeptide and/or single-chain protein and/or multi-chain protein is encoded by one or more transgenes and/or transgenic constructs that is/are selectively and/or specifically and/or exclusively expressed in one or more salivary gland cells in one or more salivary glands and secreted therefrom into the saliva, wherein in still further preferred embodiments the aforementioned peptides and/or polypeptides and/or proteins either are not present in non-transgenic naturally occurring saliva of the animal, or are present in the transgenic saliva in concentration or form or both concentration and form that does not occur in non-transgenic naturally occurring saliva of the animal.

In another aspect, the invention provides transgenic animals comprising an introduced genetic construct that alters gene expression in cells associated with saliva production. In this regard, in certain aspects and particularly preferred embodiments it is a further object of the invention to provide a transgenic animal comprising in its genome an exogenous DNA comprising (a) cis-acting transcription control regions effective for efficient transcription of operably linked DNAs in cells that secrete polypeptides into saliva, and (b) operably linked thereto, DNA encoding a polypeptide. In this regard, in certain highly particularly preferred embodiments in this regard, the polypeptide comprises a signal sequence effective for secretion of the polypeptide into the saliva of the animal.

In another aspect the invention in certain preferred embodiments provides transgenic animals that produce saliva of non-naturally occurring composition that differs from the composition of the saliva that occurs naturally in the non-transgenic animal. Further in this regard the invention provides in certain particularly preferred embodiments transgenic saliva that, as a consequence of the expression of one or more transgenes, particularly transgenes in salivary gland cells, and/or secretion of the transgene-encoded polypeptide and/or protein into the saliva: (a) comprises one or more proteins, polypeptides and/or other substances (in accordance with the foregoing descriptions) that is not a constituent of saliva that occurs naturally in the saliva of the non-transgenic animal; (b) and/or does not comprise a substance that occurs in and characterizes the saliva of the non-transgenic animal; and (c) and/or has one or more polypeptides and/or proteins and/or other substances in amounts that characteristically differ from the amounts in the saliva of the non-transgenic animal.

In another aspect, the invention provides transgenic animals that produce non-naturally occurring saliva in accordance with the foregoing, wherein in preferred embodiments the transgenic animals produce in their saliva one or more substances of interest, particularly one or more polypeptides and/or proteins of interest, especially one or more of the aforementioned polypeptides and/or proteins.

In all these regards, in preferred embodiments in accordance with each and all of the foregoing aspects and embodiments the invention provides transgenic animals that are mammals. In particular in this regard, the invention provides in further preferred embodiments in accordance with each and all of the foregoing aspects and embodiments of the invention transgenic mammals animals that produce large amounts of saliva, particularly mammalian transgenic animals that produce large amounts of saliva. In additional preferred embodiments in this regard the invention provides transgenic non-human mammals that are ruminants, particularly ruminants that produce large amounts of saliva, particularly monogastric ruminants, particularly monogastric ruminants that produce large amounts of saliva. Further, the invention provides in all these regards, in accordance with each and all of the foregoing aspects and embodiments transgenic mammals that are and/or are selected from the group consisting of murine (e.g., mouse and rat), swine, ovine, caprine, bovine and equine transgenic mammals, that in further preferred embodiments in this regard are, and/or are selected from the group consisting of, ovine, caprine or bovine transgenic mammals, and that in certain especially preferred embodiments in this regard are bovine transgenic mammals.

In all these and other regards, in accordance with each and all of the foregoing aspects and embodiments, the invention in certain preferred embodiments further provides methods for producing one or more substances of interest in saliva of transgenic animals, comprising expressing in the animal one or more transgenic constructs to provide the desired substance of interest in the animal's saliva, collecting saliva from the animal, and obtaining the substance from the saliva. In preferred embodiments in this regard, in accordance with the previously noted preferred embodiments in this regard, preferred substances are polypeptides and/or proteins, especially those encoded by one or more of the transgenic constructs, particularly polypeptides and/or proteins that undergo complex post-translational processing and modification that affects bio-activity, also particularly blood proteins, proteins of hemostasis, including regulatory, enzymatic and structure proteins involved in forming blood clots (coagulation), dissolving clots and regulating the processes of clot formation, maintenance, breakdown and removal, especially in particular von Willebrand Factor ("vWF"), fibrinogen, prothrombin and thrombin, also especially in particular albumin, antibodies, growth hormone and phytases.

In another aspect, the invention provides in certain preferred embodiments methods in accordance with the foregoing aspects and embodiments of the invention, comprising collecting saliva from one or more salivary glands of the transgenic animal, wherein in further preferred embodiments in this regard the one or more salivary gland includes or is the type of salivary gland or glands that most produce saliva in the animal, wherein in especially preferred embodiments one or more glands is one or more parotid glands, wherein further in these regards in certain preferred embodiments the saliva is collected from only one of a pair or other multiple of glands that are present in the animal, in particular in this regard from one of a pair of parotid glands in the animal.

In a related aspect in this regard, the invention provides in certain preferred embodiments methods in accordance with the foregoing, comprising obtaining saliva from the animal via a cannula placed in the lumen of one or more salivary glands, especially parotid glands, particularly in accordance with the immediately foregoing preferred embodiments. In further preferred embodiments in this regard the invention provides methods for collecting saliva from a transgenic animal, comprising collecting saliva through one or more cannula placed in lumen of one or more saliva-producing glands, especially glands that contribute most to saliva production, particularly the parotid glands, especially glands in which transgene expression and production of the transgenic product of interest is most advantageous (that is: most efficient, where it is found in the highest concentration or the most active form, or where saliva can be obtained in the greatest volume, or a combination thereof), particularly wherein more than one tube is implanted in more than one salivary gland in the animal, also wherein cannula are placed in only one member of each pair of salivary glands in the animal, further wherein saliva is collected through the cannula continuously, and in other preferred embodiments, wherein saliva is collected intermittently. The invention further provides in certain related preferred embodiments in this regard methods in which cannula are permanently placed in the glands, wherein the saliva is collected through the cannula into a collection vessel, wherein further in this regard, the collection vessel is mounted on the animal so that the animal is free ranging and in other preferred embodiments wherein saliva is collected from the animal and then transferred to a collection vessel that is not mounted thereon. In related preferred embodiments the invention further provides methods in accordance with the foregoing in which the collection vessel contains preservatives and/or protease inhibitors and/or agents that aid subsequent processes to purify the one or more substances of interest, including but not limited to immuno-affinity reagents.

In yet another aspect, the invention provides genetic constructs for making transgenic animals, as well as transgenic constructs in accordance with the foregoing. In particular, the invention provides in certain preferred embodiments in this regard transgenic constructs comprising cis-acting expression control elements together with one or more coding regions that together encode the amino acid sequence of one or more polypeptides to be expressed, wherein the expression control elements and the coding regions are combined in the construct so that, when properly incorporated, into a transgenic animal, they effectuate the synthesis of the encoded polypeptide, particularly in salivary glands of the animal and especially its secretion into the animal's saliva. Preferred embodiments in this regard as to, for instance, the encoded polypeptide, the species of transgenic animal, and the like are in all regards in accordance with the foregoing aspects and preferred embodiments. Thus, in particular, preferred embodiments of the invention in this regard provide, in accordance with each and all of the foregoing aspects and embodiments of the invention genetic and transgenic constructs that are specifically active in cells that secrete substances into saliva, and/or that are active in salivary gland cells and engender expression therein of the polypeptide of interest or of a precursor thereof and/or are effective in salivary gland cells to engender highly efficient expression and production therein of the polypeptide of interest or of a precursor thereof and/or are effective in parotid gland cells to engender highly efficient expression and production therein of the polypeptide of interest or of a precursor thereof and/or use a promoter and/or one or more other cis-acting control elements that are, that are derived from, or that are similar to the control element of one or more genes for a protein that is among the most abundant proteins in salivary gland cells and/or in saliva, in particular in this regard one of the 10 most abundant proteins in salivary gland cells and/or in saliva, yet more particularly, one of the 5 most abundant proteins in salivary gland cells and/or in saliva, and in still further preferred embodiments in this regard the most abundant or the second most abundant protein in salivary gland cells or in saliva. Among particular preferred control regions in this regard are those of genes of the multi-gene family of proline-rich proteins ("PRP"), in particular the promoters of PRP genes.

In other aspects the invention provides in certain of its preferred embodiments uses of the compositions, proteins, polypeptides, and other substances, including among others, their utilization in therapeutic compositions and/or formulations for clinical use in human and veterinary health care and treatment; in cosmetic compositions and/or formulations, in compositions and/or formulations for environmental applications, such as remediation, and in other compositions and/or formulations in which any compositions, proteins or other polypeptides and other substances in accordance with the invention as described herein can be usefully employed.

In brief summary, the invention relates in some aspects, to the production of non-naturally occurring saliva in genetically engineered animals, and to the production in the non-naturally occurring saliva of desired substances. In addition, in some aspects the invention relates also to animals genetically engineered to produce non-naturally occurring saliva, to the non-naturally occurring saliva thus produced, and to non-naturally occurring compositions made with or derived from the saliva. In certain further aspects the invention relates further to animals genetically engineered to produce non-naturally occurring constituents in their saliva, to non-naturally occurring compositions made with or derived from the saliva, and to the non-naturally occurring constituents of the saliva thus produced. In certain particular embodiments in this regard, the invention relates to the animals genetically engineered to produce in their saliva polypeptides that differ in amount, modification, processing, complexation, primary, secondary, tertiary or quaternary structure, or nature from the polypeptides of naturally occurring saliva, to compositions comprising the polypeptides made with or derived from the saliva thus produced, to compositions comprising the polypeptides thus produced, and to the polypeptides themselves. The invention relates in some of its further aspects in accordance with the foregoing: to methods for genetically engineering animals to produce altered saliva in accordance with the foregoing; to methods for obtaining saliva from the genetically engineered animals, to methods for making with or deriving from saliva in accordance with the foregoing desired compositions, products and/or compounds; to methods for processing such compositions, products and/or compounds, and to methods for using them. In yet further aspects, the invention relates to the production of desired substances by genetic engineering of animals to express the substance in advantageous amount and form, specifically and/or exclusively in their saliva, particularly animals that produce copious amounts of saliva. In certain preferred embodiments in accordance with the foregoing the invention relates as well to the production of desired polypeptides, especially in the saliva of livestock animals that produce saliva in large volume, most especially in cows.

Other objects, features and advantages of the present invention will become apparent from the following description and specific examples. It is to be understood, however, that the description and the specific examples, while indicating preferred embodiments of the invention, are given by way of illustration only, since various changes and modifications within the spirit and scope of the invention will become apparent to those skilled in the art from this the foregoing background and summary, from the description and the examples, and from the entirety of the disclosure.

Terms

The following explanations are provided as an aid to the reader in developing an understanding of a number of the terms and phrases as they are used in the description herein of the presently disclosed invention. They are provided to facilitate greater clarity in understanding the invention and its scope. They are provided by way of illustration, however, and they do not, in and of themselves, define the invention per se or any of its limitations. Rather, they are provided as usefully supplemental to the description of the invention provided in the other parts of the present disclosure.

Bioactive The term "bioactive" as used herein means "biologically active;" "having one or more activities of biological significance," "able to carry out one or more activities and/or biological functions," and the like.

Commercially advantageous The term "commercially advantageous" as used herein means "perceived by a business as furthering a commercial business goal." Commercially advantageous undertakings in accordance with the meaning given the term in this disclosure is not limited to profitable undertakings: it also includes activities undertaken to achieve commercial goals that, by themselves, may not be profitable.

Economically viable The term "economically viable" means, as used herein, an undertaking or enterprise that is perceived to be financially rational i.e., it is expected to and/or actually generates net positive revenues.

Engender The term "engender" in the context of this application refers to any case in which the regulatory regions are operably linked to the sequences to be expressed (coding sequences) so that the desired gene expression product will be produced in the organism. As used herein in this context the term encompasses not only the introduction into the organism of a construct in which control signals are operably linked to a structural gene encoding a polypeptide to be expressed, but also the integration, by either homologous or non-homologous into the host cell genome of one or more exogenous regulatory sequences in such a manner that they become operably linked to an endogenous expressible sequence, such as a coding sequence for the polypeptide and/or protein of interest, and thereby engender expression of or contribute to causing the expression of (as by an enhancer sequence) a desired endogenous sequence (preexisting in the genome prior to introduction of the exogenous sequence). By "significant" is meant that the polypeptide and/or protein of interest can be recovered from the transgenic organism in amounts useful for research or for commerce or both.

Operably Linked, in Operable Linkage and the Like

As used herein the terms "operably linked," "in operable linkage" and the like generally refer to genetic elements for expressing genes and mean that the elements are linked together so that they can operate properly with one another and thereby effectuate a desired function, typically tissue-specific expression of a gene and, as to the present invention generally, the production of a desired substance in saliva of a transgenic animal containing the construct formed of the operably linked elements.

Polypeptide(s) and/or protein(s) The terms "protein," "polypeptide," "peptide" and "oligo-peptide" generally are used herein consistent with their art with recognized meanings as follows.

(1) "Peptides" and "oligopeptides" denote short polypeptides. Short polypeptides are included in the meaning of the term "polypeptide," as used herein.

(2) The term polypeptide as used herein generally means an unbroken chain of amino acids within which each amino acid is joined by a peptide bond to the immediately preceding and to the immediately subsequent amino acid in the chain {except for the first amino acid (generally referred to as the amino-terminal amino acid) and the last amino acid in a chain (generally referred to as the carboxyl terminal amino acid) are immediately adjacent to only one other amino acid and therefore have only one peptide bond). Natural polypeptides are linear and unbranched as a rule; but, not always. Branched polypeptides and cyclic polypeptides occur naturally as well, and are included in the meaning of the term as used herein. Naturally occurring polypeptides almost exclusively contain a mixture of just 20 amino acids that predominate in this regard in virtually every living organism that has been examined. Nonetheless, polypeptides in nature undergo a wide variety of covalent modifications and contain thereby a wide variety of covalently modified amino acids. The term "polypeptide," as used herein, includes all forms of covalently modified polypeptides in this regard as well. Polypeptides, particularly those longer then a dozen or so amino acids, generally assume particular, complex conformations in solution, as a result of interactions with the solvent and as a result of intramolecular interactions between different regions of the polypeptide itself. Under physiological conditions, conformation-determining solvent and intramolecular interactions generally involve non-covalent bonding interactions; but, covalent bonds also play an important role in polypeptide folding, primarily S—S bonding between cysteine residues. The term polypeptide as used herein includes polypeptides with any and all structural conformations.

(3) Proteins primarily are composed of one or more polypeptides. Some are, quite simply, a single polypeptide chain. Others are a single polypeptide chain bonded non-covalently, or covalently, to one or more other "factors," or "co-factors," such as metal ions, heme, and the like. Proteins made of a single polypeptide, associated or not with additional factors, are referred to as "single-chain proteins" and similar terms herein. Commonly, proteins are composed of two or more polypeptides. Proteins with several polypeptide chains, whether or not associated with additional factors, are referred to herein as "multi-chain" proteins and similar terms. The polypeptides that make up a multi-chain protein may be all the same, or they may be different. Moreover, many proteins (both single chain and multi-chain) undergo processes of maturation during synthesis and/or activation processes that involve one or more steps of proteolytic cleavage. Initially intact polypeptides, as a result, are broken into several fragments. Some fragments remain in the protein (or are the protein, in the case of single chain proteins). Other fragments are released. As used herein, the term "protein" includes all of the foregoing forms and varieties of single and multi chain proteins, including inter alia, those not associated with other factors and those that are, those that are intact as initially synthesized, and those that have been fragmented as a result of proteolytic steps of processing, maturation and/or activation. Also included in the meaning of the term as used herein are the aforementioned polypeptides in their forms.

(4) The structural sequences of genes linearly encode the amino acids of polypeptides, notwithstanding the fragmented nature of eukaryotic structural genes in which the coding regions are broken up into smaller "exons" of coding sequence separated by non-coding "introns." Genes are expressed by (a) transcription, in which the DNA is sequence is copied into mRNA and (b) translation, in which the mRNA sequence directs the sequence of amino acids during polypeptide/protein synthesis. Although genes linearly encode polypeptides, a given gene may encode several different polypeptides as a result of alternative transcript splicing. And a single polypeptide may give rise to several polypeptides as a result of proteolysis occurring during processing and activation. Moreover, single polypeptide products of a single gene frequently self associate to form homo-dimer and higher homo-multimer multi-chain proteins. As used herein, the terms polypeptide and protein are used herein to include single polypeptide chains and proteins composed of one or more polypeptides of all such genetic and/or cellular origins and/or processes in this regard.

(5) As the foregoing makes clear, there is considerable overlap in some regards between the subject matter denoted by the terms "polypeptide" and "protein." The present invention involves transgenic expression to produce substances in saliva in transgenic organisms. In certain particularly preferred embodiments in this regard, the products are the direct result of transgene expression, initially polypeptides, but often proteins, particularly homo-multimers, formed by the polypeptides. To denote the inclusion of both polypeptides and proteins in the invention in this regard, and to avoid the potential for ambiguity in this regard that might result from using one term or the other, whether systematically or not, the phrase polypeptide and/or protein has been used herein to indicate that the invention generally relates to and encompasses transgenic production of both the polypeptides encoded by expressed transgenes, and the single and multi-chain proteins produced by self association of one or more types of polypeptides produced by expression of one transgene or more than one transgene.

Pharmaceutical polypeptide and/or protein The term "pharmaceutical" is used herein to refer to polypeptides and/or proteins usefully employed to treat disorder or disease in subjects, notably human patients.

Proactive The term "proactive" is used herein to refer to forms of substances in which one or more activities is blocked and inactive; but, can be "unmasked" thereby to release a form of the substance with the previously blocked activity.

Probioactive The term "probioactive" is used herein to mean that one or more biological activities of a substance is reversibly inactivated. The activities are "masked" as it were, but the masking can be removed, and the bioactive substance thus regenerated.

Regulatory regions The term "regulatory regions" also may be referred to herein as "control regions," "regulatory elements," "control elements," "regulatory sequences" and similar terms. The term "cis-acting" element," also referred to as "cis-acting" regulatory element," and "cis-acting control element" each denotes a genetic element that controls function, in this case gene expression, i.e., a region of the genome, part of the DNA, that effectuates control, in contrast to other elements of control, such as proteins, that are not part of the DNA per se and thus are referred to as "trans-acting" factors.

Significant Amount, Significant Quantity and the Like

The terms "significant amount," "significant quantity" and the like when referring to the amount of gene expression, or polypeptide and/or protein and/or other substance of interest in saliva, and/or that can be recovered from the saliva, and the like, means amounts useful for research or for commerce or both.

Specifically The term "specifically" as used with reference to gene expression herein means that the gene is very considerably more active in the indicated cells, gland, tissue, compartment, etc. than in other cells, glands, tissues, compartments, and that cumulative non-specific expression elsewhere does not deleteriously affect the host animal, and generally is diffuse, if it exists at all. However, specific expression in one cell, gland, etc. is a matter of predominance, not necessarily exclusivity. Thus, as the term is meant herein, it can be used to say that "the WAP promoter is expressed specifically in mammary gland epithelial cells and thus it is useful to produce transgenic proteins specifically in transgenic milk" although the WAP promoter also is active at a very much lower level of expression in salivary glands.

Substantially the same The phrase "substantially the same" as used herein means that the subject of the phrase is almost, nearly, virtually or actually the same as the object of the phrase with regard to the characteristic(s) being discussed. Particularly, the phrase is used to denote close similarity without implying absolute identity. Thus, for instance, a protein produced in transgenic saliva that is substantially the same in its characteristics as its naturally occurring counterpart, nevertheless may have some specific features that alter it in minor, perhaps subtle ways and that thus distinguish it structurally and/or functionally from its natural counterpart. For instance, the phrase "substantially the same glycosylation," while it includes identity in some or even in all characteristics of glycosylation, also contemplates minor qualitative and/or quantitative differences in glycosylation characteristics, such as differences in the exact extent of glycosylation, or the exact composition or structure of the glycans, or variations in the distribution of glycan structures in heterogeneous populations of molecules being compared. It will be appreciated that the differences contemplated by the phrase vary with the characteristic in accordance with the variation that is expected by those of skill as to the particular characteristic in question. The phrase does not contemplate within its intended scope differences that result in dramatic differences in structure and/or function. For example, it does not contemplate differences in protein structure that obviate established purification techniques and require that new ones be developed, and it does not include differences in protein function that require major changes in end uses, or those that preclude them.

Transgene The term "transgene" means A gene in an organism that contains one or more genetic elements introduced from an exogenous source. The transgene may be entirely of exogenous origin, which often is true of expression cassettes.

DESCRIPTION

Notwithstanding the apparent disadvantages of currently available methods for obtaining substances by genetically engineering animals to produce them, the present invention provides, among other things: methods, genetic constructs, transgenic animals and devices for producing desired substances in useful amounts and forms from transgenic saliva. It provides transgenic saliva comprising one or more desired substances of interest; and compositions derived from the saliva; it provides non-naturally occurring compositions, substances and/or compounds isolated from transgenic saliva. It provides useful applications of the foregoing methods, constructs, animals, devices, compositions, substances and compounds. And it provides a great many other things that will become clear to those of skill in the art upon reading the present disclosure.

In particular, in all these regards and in other aspects of the invention further disclosed herein below, in certain of its preferred embodiments, the invention provides transgenic ruminant animals, particularly monogastric ruminants that produce large volumes of saliva, especially bovine animals, genetically engineered to produce in their saliva certain desired polypeptides and/or proteins of interest in amounts and forms useful for research or for commerce or both. Further related preferred embodiments of the invention provide methods for making transgenic cows that express the desired polypeptide in their saliva, genetic constructs for engineering efficient salivary gland expression of desired polypeptides, methods for genetically engineering transgenic bovine animals that produce the desired polypeptide in their saliva, methods and devices for collecting and processing saliva from the transgenic bovine animals to make compositions comprising the desired polypeptide of interest, non-naturally occurring compositions derived from the saliva comprising the desired polypeptide of interest, non-naturally occurring polypeptides in purified form derived from the saliva, useful formulations comprising the compositions of the purified polypeptide, and useful applications of the compositions and the purified polypeptides.

The methods, constructs, animals, devices, compositions, polypeptides, proteins, substances, compositions, formulations, uses, applications and other features of the present invention are illustrated by the description and specific examples set out in this disclosure. The disclosure, needless to say, does not and, indeed, cannot, set out completely and exhaustively all ramifications, aspects and embodiments of the invention. Nonetheless, by way of the exemplary description and examples, the general scope of the invention and much of its details will become clear to those of skill in the art.

Saliva-Specific Transgenic Expression

A variety of methods as described herein can be used to genetically engineer salivary gland-specific expression in accordance with the invention to produce saliva of non-naturally occurring composition, to produce substances of interest in transgenic saliva and to produce saliva of desirable properties, particularly for the production of polypeptides and/or proteins therein and therefrom. Some information on saliva-specific expression is provided by reference to the following publications, as explained in greater detail further below.

Mikkelsen and co-workers described techniques for manipulating gene expression in a transgenic animal to engender secretion of a gene product into saliva suitable for use in certain aspects of the present invention for production of desired substances in saliva of genetically engineered animals. See in this regard Mikkelsen at al. (1992), *Nature* 20(9): 2249-2255, which is incorporated herein by reference in its entirety in parts pertinent to genetically engineering salivary-gland specific expression of genes in animals and the secretion of desired substances thereby into saliva of the genetically engineered animals. In particular, in much the same manner as described by Mikkelson et al., salivary-gland specific expression can be engineered using transcription control regions of genes that encode especially abundant proteins of salivary gland cells or of saliva itself. In particular in this regard, expression control regions from the gene for parotid secretory proteins ("PSP") generally are suitable to engineer salivary-gland specific gene expression, in the manner Mikkelsen and co-workers used control regions from the gene for mouse PSP ("moPSP") to engender parotid-specific transgenic expression in mice. The mouse PSP gene has been cloned and characterized by Shaw and Schibler, and by Poulsen and co-workers. (See in this regard, Shaw and Schibler (1986), *J Mol Biol* 192: 567-576 and Poulsen et al. (1986), *EMBL J*. 5: 1891-1896, which are incorporated herein by reference in their entirety particularly as to transgenic salivary gland-specific expression.) The region of 5' flanking DNA required for salivary gland-specific expression is about 4.6 kb; but, longer regions, extending farther upstream may provide higher levels of expression. In the mouse system, notably, the transcription control regions for parotid gland-specific expression differ from those for sublingual gland-specific expression. The general organizational schema of the transcription control regions necessary and sufficient for specific and efficient transgenic expression in salivary gland cells in mice fits the general organizational model of transcription control regions of other genes with tissue-specific patterns of expression. Accordingly, the PSP paradigm for salivary gland-specific expression in mice can be followed to isolate the genetic elements for efficient, salivary gland-specific expression in other animals. Furthermore, in accordance with some preferred embodiments of the invention wherein endogenous transcription control regions are to be employed, cloned PSP genes of mice (for instance) can be used to isolate homologs endogenous to the desired host animal. The transcription control regions of the host-endogenous genes then can be characterized and, as needed, recombined with other DNA and/or modified for use to make a gene expression construct for microinjection into a host. The techniques required generally are routine to those of skill in the pertinent art, and they have been used for this purpose successfully in the past, as described in the following publications.

Larson and co-workers also reported salivary gland expression of exogenous gene constructs in transgenic mice. See Larson et al. (1994), *Transgenic Research* 3(5): 311-316, which is incorporated herein by reference in its entirety particularly in parts pertinent to genetic engineering salivary gland-specific expression of genetic material in transgenic animals. Larson et al. describe, among other things, a 7.1 kb mini-gene construct suitable for efficient salivary gland-specific expression of transgenes in mice. Expression using this construct was much greater than 1% of endogenous expression levels exhibited by the 6.2 kb promoter region previously used to engender salivary-gland specific expression.

Mirels and co-workers characterized the genes for rat salivary-gland B1-immunoreactive proteins of adult (and neonatal) rat sublingual and parotid glands (often referred to as the B1-IPs), that also are the major secretory products of rat submandibular gland acinar-cell progenitors. The transcription control elements of these genes, and their homologs and paralogs are suitable to engineer salivary gland, sublingual gland and/or parotid gland-specific expression of genes in accordance with certain aspects of the present invention in this regard. See, pertinent thereto, Mirels et al. (1998), *Biochemical Journal* 330 (Part 1): 437-444, which is incorporated herein by reference in its entirety in parts pertinent to genetically engineering specific expression of genes in animals and the secretion of desired substances thereby into saliva of the genetically engineered animals.

Constructs for Transgenic Expression in Saliva

Certain aspects of the invention relate to the introduction into organisms of genetic constructs that engender the production of a substance or substances of interest in saliva. Such constructs are referred to as, among other things, transgenic elements, transgenes, introduced genes, introduced genetic elements, exogenous genes, exogenous genetic elements, exogenously derived genetic elements and the like. As noted in greater detail elsewhere herein such elements may encode the expressed polypeptide, they may alter the control of expression of a polypeptide in the host, they may alter the amino acid sequence of the polypeptide in the host or a combination of these, among others. They have as a general property, as to the present invention, that they alter gene expression in cells of the transgenic host and thereby change the composition of the host's saliva, in particularly by engendering the production in the saliva of polypeptides and/or proteins and/or other substances of interest that differ from the substances ordinarily and/or naturally found to occur in the host's saliva, in kind and/or in amount and/or in both kind and amount, as set out in greater detail elsewhere herein.

Among substances of interest preferred in the invention in this regard are probioactive proteins (including single chain probioactive proteins and multi-chain probioactive proteins), other probioactive polypeptides, bioactive proteins, (including single chain bioactive proteins and multi-chain bioactive proteins), and other bioactive polypeptides. Further preferred in this regard are pharmaceutically active proteins and other pharmaceutically active polypeptides useful in clinical and veterinary applications and treatments, precursors of pharmaceutically active proteins and precursors of other pharmaceutically active polypeptides. Particularly preferred in this regard are probioactive pharmaceutical proteins (including single chain probioactive pharmaceutical proteins and multi-chain probioactive pharmaceutical proteins), other probioactive pharmaceutical polypeptides, bioactive pharmaceutical proteins (including single chain bioactive pharmaceutical proteins and multi-chain bioactive pharmaceutical proteins), and other bioactive pharmaceutical polypeptides.

Also among particularly preferred embodiments of the invention in these regards are (and/or are selected from the group consisting of) phytases, antibodies, growth hormones, and blood proteins including, but not limited to, serum albumin and proteins of hemostasis and/or thrombosis, especially in this regard fibrinogen, prothrombin, thrombin and von Willebrand Factor ("vWF"), and precursors thereof, very especially in this regard human fibrinogen, human prothrombin and human thrombin and precursors thereof.

Among the genetic constructs and the like that are useful in the invention in this regard are polynucleotide constructs that provide a DNA sequence encoding the polypeptide of interest or a precursor thereto operably linked to cis-acting signals necessary for expression in a transgenic organism and, in certain preferred embodiments, for transport of a translation product encoded by the construct into a particular compartment of the organism, namely in this regard, saliva.

Among preferred polynucleotides for constructs in preferred embodiments of the invention are DNA or RNA:DNA hybrids. Among particularly preferred embodiments in this regard are DNA polynucleotides. In certain preferred embodiments of the invention in this regard, DNAs that comprise regions of cis-acting transcription controls for gene expression in salivary gland cells operably linked to a region or regions encoding a polypeptide and/or protein of interest, as particularly as described elsewhere herein, very particularly, for instance human fibrinogen, human prothrombin and human thrombin. DNA-DNA hybrids are similarly preferred in some embodiments in this regard. Also useful in this regard are constructs that engender non-natural expression of genes for one or more proteins or polypeptides of interest, including preferred polypeptides and/or proteins described elsewhere herein, such as, for instance, phytases, antibodies, growth hormones, and blood proteins including, but not limited to, serum albumin and proteins of hemostasis and/or thrombosis, especially in this regard fibrinogen, prothrombin, thrombin and von Willebrand Factor ("vWF"), including precursors and other related polypeptides, very especially in this regard human fibrinogen, human prothrombin and human thrombin and precursors and related polypeptides thereof. Also especially preferred in this regard are constructs that are stably incorporated in the genome of germ line cells of the mature organism and inherited in normal, Mendelian fashion by reproduction thereof. Constructs that comprise an operable signal sequence that effectuates transport into saliva are further preferred in the invention in this regard.

The constructs may be one polynucleotide or several polynucleotides when introduced into a cell or embryo or the like to form a transgenic animal in accordance with the invention. Particularly preferred are single chain, double-stranded DNA polynucleotides in this regard. Also preferred are DNA-RNA hybrid polynucleotides. When more than one polynucleotide is used in this regard, they generally combine with one another and/or with endogenous genetic elements of the host organism, as a result of in vitro or in vivo processes, to form a construct that then engenders transgenic expression of the polypeptide of interest in the host organism, particularly in salivary gland cells, especially parotid gland cells, most especially epithelial cells of parotid glands that secrete efficiently into the lumen of the gland and thus into the saliva.

In certain particularly preferred embodiments of the invention, preferred constructs provide a polynucleotide sequence encoding a particular polypeptide of interest or a related polypeptide operably linked to the cis-acting signals necessary for expression in mammary gland cells and for secretion into saliva of a non-human transgenic mammal. Particularly highly preferred in this regard are cis-acting signals that provide efficient expression in salivary gland cells and secretion into saliva of the polypeptide in a form that preserves its native activity with little or no expression elsewhere in the organism, as described in greater detail elsewhere herein. DNA and RNA:DNA hybrids are particularly preferred polynucleotides in this regard. DNA is especially preferred.

Cis-Acting Sequences for Transgenic Expression

A wide variety of genes have been expressed in a wide variety of transgenic organisms. Many blood proteins in particular have been expressed in animals. Moreover, transgenic expression of blood proteins has been targeted to specific compartments. The cis-acting controls used in the past to express blood proteins in transgenic organisms also are useful, in many cases, in expressing polypeptides and/or proteins of interest, such as the polypeptides and/or proteins of preferred embodiments of the invention herein disclosed, in transgenic organisms in accordance with the present invention. Examples in this regard are described in Lubon et al., *Transfusion Medicine Reviews X*(2): 131-141 (1996) which is incorporated by reference herein in its entirety. Some preferred embodiments relating to expression-regulatory regions for transgenic expression of preferred polypeptides and/or proteins described elsewhere herein are discussed in further detail below.

Promoters and Other Expression Control Sequences

The cis-acting regulatory regions useful in the invention include the promoter used to drive expression of a gene in a transgenic organism effective for the production in the organism of polypeptides and/or proteins of interest. Preferred in this regard are regulatory regions that engender the production of significant amounts of the polypeptide and/or protein of interest that can be recovered from the organism, purified and, where required, such as for probioactive proteins and other probioactive polypeptides of certain of the preferred embodiments of the invention in this regard, converted from the probioactive form to the bioactive form. The term "engender" in this context refers to any case in which the regulatory regions are operably linked to the sequences to be expressed (coding sequences) so that the desired gene expression product will be produced in the organism. As used herein in this context the term encompasses not only the introduction into the organism of a construct in which control signals are operably linked to a structural gene encoding a polypeptide to be expressed, but also the integration, by either homologous or non-homologous into the host cell genome of one or more exogenous regulatory sequences in such a manner that they become operably linked to an endogenous expressible sequence, such as a coding sequence for the polypeptide and/or protein of interest, and thereby engender expression of or contribute to causing the expression of (as by an enhancer sequence) a desired endogenous sequence (preexisting in the genome prior to introduction of the exogenous sequence). By "significant" is meant that the polypeptide and/or protein of interest can be recovered from the transgenic organism in amounts useful for research or for commerce or both.

Particularly preferred are regulatory regions that provide for the production of significant amounts of the protein, polypeptide or other substance of interest in salivary glands, especially parotid glands, most especially in saliva, in particular in animals that produce copious amounts of saliva, especially in this regard in cows. Particularly useful regulatory regions for expression in saliva are promoters that are active in cells of salivary glands and other tissues that secrete into saliva, in particular in this regard in parotid gland cells that secrete into saliva, especially epithelial cells of parotid glands that secrete polypeptides into saliva, particularly, as set out elsewhere herein, in animals that produce large amounts of saliva, particularly in monogastric ruminant animals, especially porcine, caprine, ovine, bovine and/or equine animals, very especially bovine animals. Especially useful in this regard are regulatory regions that are specifically active in the aforementioned cells; i.e., that are more active in the aforementioned cells and tissues than in other tissues under physiological conditions where saliva is synthesized. Typically the regulatory regions are much more active in the specific cells and tissue than in any other cells or tissues. Generally, as used herein, highly preferred are promoters and other regulatory elements that are both specific to and efficient for expression in cells that secrete into saliva, particularly cells of salivary glands, particularly epithelial cells proximal to the lumen of salivary glands, particularly as well salivary gland cells that secret polypeptides and other substances into saliva, particularly further still cells that secrete into and largely determine and control the composition of saliva, particularly in animals that produce large amounts of saliva, especially particularly, as set out elsewhere herein, in animals that produce large amounts of saliva, particularly in monogastric ruminant animals, especially porcine, caprine, ovine, bovine and/or equine animals, very especially bovine animals and/or cows. By "efficient" is meant that the promoters are strong promoters in cells of salivary glands, that they engender the synthesis of large amounts of protein therein, particularly in cells that efficiently secrete the protein into saliva, especially in cows. Promoters and other regulatory elements for making genetic and/or transgenic constructs that can be used to produce polypeptides and/or proteins in salivary gland cells and in saliva of transgenic mammals in accordance with the invention herein disclosed can be obtained by methods well known and readily available to those of skill in the cloning arts. Among preferred promoters and other regulatory elements for salivary gland-specific expression are the promoters and other regulatory regions of genes that are expressed at high level in salivary gland cells, especially those expressed the most in salivary gland cells, particularly parotid gland cells. (The term "regulatory regions" also may be referred to herein as "control regions," "regulatory elements," "control elements," "regulatory sequences" and the like).

It is understood that the invention encompasses both constitutive and inducible promoters. Among preferred promoters in this regard are inducible promoters, particularly those that are inducible in cells of salivary glands and cells of any other tissues that secrete substances into saliva, such as those that are induced by hormones or those that can be induced by hormones or other substances included in feed or in drinking water or other fluids. A wide variety of constitutive and inducible promoters are known that can be used in this regard, including as well as those above, those that can be induced by hormones, ligands and metals. A variety of such promoters, their inducible elements, and their induction are described in for example, Sambrook et al. *Molecular Cloning: A Laboratory Manual*, $2^{nd}$ Ed., Cold Spring Harbor Laboratory Press, Cold Spring Harbor, N.Y. (1989), which is incorporated herein by reference in its entirety particularly as to parts pertinent to promoters and induction.

Among the sequences that regulate transcription that are useful in the invention, in addition to the promoter sequences discussed above, are enhancers, splice signals, transcription termination signals and polyadenylation sites, among others. Particularly useful regulatory sequences include those that increase the efficiency of expression of the polypeptide and/or protein of interest in transgenic organisms. Also particularly preferred in this regard are those that increase the specificity of expression in targeted compartments of a transgenic organism. Among highly particularly preferred regulatory regions in this regard are those that increase the efficiency, the specificity or both the efficiency and the specificity of expression in salivary glands, and the production of a desired substance thereby in the saliva of transgenic non-human animals in accordance with the invention.

3' Untranslated Sequences

Also among regulatory sequences preferred in certain embodiments of the invention are sequences comprised in the 3' untranslated portion of genes that increase expression of transgenicly-encoded products particularly in salivary gland cells of transgenic non-human mammals, especially those that increase the amount of the product secreted into saliva. Among highly preferred sequences in this regard are those that stabilize mRNA transcribed from transgenes. Among preferred embodiments in this regard are sequences that comprise a polyadenylation signal, particularly the polyadenylation signal of SV40. Among preferred regions of this type are those derived from the genes for proteins that are expressed at high levels in parotid gland cells.

Trafficking and Translational Signals

Also important to the invention are signal sequences that can direct secretion of proteins into the saliva of transgenic animals. In this regard, both endogenous and heterologous signal sequences are useful in the invention. Generally, the signal peptides of proteins normally secreted into saliva are particularly useful in the invention in this regard. The signal sequences of proteins that occur in high concentration in saliva are particularly preferred.

Among the sequences that regulate translation and transport, in addition to the signal sequences discussed above, are ribosome binding sites and sequences that augment the stability of mRNA. Also, especially useful in the present invention are sequences that advantageously modulate post-translational modifications in accordance with the invention herein described.

Gene Activation

Changes in gene expression also can be engineered in transgenic animals without using a complete structural gene sequence. Perhaps most notably in this regard, the expression of endogenous genes can be activated—or altered in other ways—by recombination in situ in a host cell between an exogenous DNA and the target gene. The recombination event removes inactive endogenous expression controls and leaves active expression controls in their place. Gene activation methods can be applied to engender expression of any "endogenous" gene, i.e., any gene in the genome at the time of recombination: not only native genes but also of one or more previously modified native genes and/or one or more transgenes previously integrated into the host. Perhaps needless to say, the previously integrated transgenes in this regard may be of entirely heterologous origin, or may be chimeric genes (containing some regions(s) endogenous to the host and others from heterologous sources), or may be almost entirely, or entirely in some methods, endogenous to the host (for instance, a native structural gene of the host linked to 3' and 5' flanking regions derived from different host genes. Gene activation methods can be used to make transgenic animals by altering the genome and gene expression of germ cells, embryonic cells and/or somatic cells. Techniques in this regard are described in, for example, WIPO International Publications numbers WO 93/09222 and WO 91/12650, and U.S. Pat. No. 5,641,670, each of which is incorporated herein by reference in its entirety in parts pertinent to in situ gene activation methods for use in the present invention. As described therein and elsewhere, specific polynucleotide sequences corresponding to regions of a target gene, such as polypeptides and/or proteins of preferred embodiments of the invention herein disclosed, or to regions proximal or distal thereto, are used to target integration of an exogenous construct into a specific site in a genome by homologous recombination of the specific sequences in the construct with their counterparts in the target site. Specific expression-regulatory sequences can be integrated into genomes in this way to control expression of specific genes. The methods can be used to turn targeted genes on or turn them off or to alter their regulation in a cell. Accordingly, these methods can be used to engender production of desired polypeptides and/or proteins in cells in which it is not ordinarily produced, or to increase expression in cells that normally produce it at low levels. These methods also can be used to introduce specific mutations into a gene. By these means specific mutations can be introduced into coding regions of endogenous genes, such as those that encode functional regions of the protein.

In some cases, cells that can be manipulated in this way can be used to make transgenic organisms, although such methods are not available currently for all organisms. In one embodiment in this regard, for example, a DNA encoding a human polypeptide and/or protein of interest can be introduced into a transgenic animal and subsequently modified therein as described above. Alternatively, a cell can be thus modified in vitro to express the polypeptides and/or proteins of interest. Subsequently, the cell can be introduced into an animal, preferably into the major secretory salivary gland, preferably, in accordance with various preferred embodiments in this regard further disclosed elsewhere herein, into the parotid gland in non-human mammals that produce large amounts of saliva, in particular amounts sufficient for commercially advantageous and/or economically viable production of substances from the saliva, especially transgenic polypeptides and/or proteins, further especially in this regard monogastric ruminant non-human mammals that produce the aforementioned sufficient amounts of saliva, also further especially in this regard porcine, ovine, caprine, bovine and/or equine animals that produce the aforementioned sufficient amounts of saliva, particularly especially bovine animals in this regard.

In an illustrative embodiment in this regard, the host cell can be a fertilized oocyte or embryonic stem cell that can be used to produce a transgenic animal containing a gene encoding a polypeptide and/or protein of interest. Alternatively, the host cell can be a stem cell or other early tissue precursor that gives rise to a specific subset of cells that can be used to produce transgenic tissues in an animal.

Making Transgenic Organisms

Transgenic organisms that express a polypeptide and/or protein of interest may be produced in accordance with the invention described herein using many well-known techniques, such as those described in GENETIC ENGINEERING OF ANIMALS, Ed. A. Puhler, VCH Publishers, New York (1993), in more detail in Volume 18 in Methods in Molecular Biology: TRANSGENESIS TECHNIQUES, Eds. D. Murphy and D. A. Carter, Humana Press, Totowa, N.J. (1993), and in Lubon et al., (1996), *Transfusion Medicine Reviews* X(2): 131-141, each of which is incorporated herein by reference in their entireties particularly as to the foregoing in parts pertinent to methods for making transgenic organisms in general, and to methods useful for making transgenic organisms that produce substances in their saliva, particularly polypeptides and/or proteins.

In particular, transgenic animals, such as murine (mouse and rat), swine, ovine, caprine, bovine and equine animals, that produce saliva of altered composition, such as transgenic animals that produce in their saliva a desired substance not naturally occurring therein in accordance with certain preferred embodiments of the invention, can be produced using methods described, in among others: MANIPULATING THE MOUSE EMBRYO, Hogan et al., Cold Spring Harbor Press, Cold Spring Harbor, N.Y. (1986); Krimpenfort et al. (1991), *Bio/Technology* 9: 844 et seq.; Palmiter et al. (1985), *Cell* 42: 343 at seq.; GENETIC MANIPULATION OF THE EARLY MAMMALIAN EMBRYO, Kraemer et al., Cold Spring Harbor Press, Cold Spring Harbor, N.Y. (1985); Hammer et al., (1985), *Nature* 315: 680 at seq.; U.S. Pat. No. 4,873,191 of Wagner et al., *Genetic Transformation of Zygotes*, and U.S. Pat. No. 5,175,384 of Krimpenfort at al., *Transgenic Mice Depleted in Mature T-Cells and Methods for Making Transgenic Mice*, each of which is incorporated herein by reference in its entirety particularly as to the foregoing in parts pertinent to producing transgenic mammals by introducing DNA or DNA:RNA constructs for polypeptide and/or protein expression into cells or embryos. (Regarding DNA:RNA constructs and their use see for instance U.S. Pat. No. 5,565,350 of Kmiec, *Compounds and Methods for Site Directed Mutations in Eukaryotic Cells* and U.S. Pat. No.

5,756,325 of Kmiec, *Compounds and Methods for Site Directed Mutations in Eukaryotic Cells*, each of which is incorporated by reference herein in its entirety particularly as to the foregoing in parts pertinent to targeted genetic manipulations useful to produce transgenic organisms in accordance with the present invention.

Thus, for example, transgenic organisms of the present invention can be produced by introducing into eggs or developing embryos one or more genetic constructs that engender expression of one or more polypeptides and/or proteins of interest. Well known and readily available methods generally can be used for introducing genetic material into cells and/or for altering endogenous genetic material for making transgenic organisms in accordance with the invention. Among useful techniques in this regard are those for introducing genetic constructs and/or other genetic or genome altering DNA, RNA, PNA or other substances by injection, by infection, by transfection, such as calcium phosphate transfection, by means of cationic reagents, by using sperm or sperm heads or the like, by lipofection, by liposome fusion, by electroporation, and by ballistic bombardment, among other well known techniques useful for this purpose. New techniques that may be developed in this regard also will be recognized when they become available as being useful for introducing genetic material or altering endogenous genetic material in accordance with various aspects and embodiments of the invention herein described.

Useful techniques in this regard include those that involve integration of exogenous genetic material into the host cell genome by homologous recombination, such as those that can be employed to achieve targeted integration, and those that involve non-homologous integration. While stable integration of genetic material into the host genome is preferred in certain aspects and embodiments of the invention, methods that provide stable genetic alterations by means of extra-chromosomal elements also are useful in certain aspects and embodiments of the invention, as are methods that provide transient incorporation into and/or alteration of host cell genetic material and/or transient alteration of introduced genetic constructs and/or transient alteration of host cell gene expression and/or protein synthesis.

It will be appreciated that the foregoing is provided as being illustrative of the many well known and available methods that can be used by those of skill in the pertinent art to make transgenic animals in accordance with the present invention, in particular to make transgenic animals in accordance with the present invention that express a transgene in salivary gland cells and thereby produce a substance of interest in the animal's saliva, in particular a polypeptide and/or protein of interest, further particularly wherein the salivary gland cells are cells of the parotid gland and the cells continuously secret the polypeptide and/or protein into the gland duct and thereby into the saliva.

Using these methods and others, constructs can be introduced into pluripotent cells, totipotent cells, germ line cells, eggs, embryos at the one cell stage, embryos at several stages of greater numbers of cells, and cleavage stage embryos, among others, to make transgenic organisms of the invention. In these regards, among others, they may be introduced by such methods in pronuclei, nuclei, cytoplasm or other cell compartments or into extracellular compartments of multicellular systems to make transgenic organisms of the invention.

In a preferred method, developing embryos can be infected with retroviral vectors and transgenic animals can be formed from the infected embryos. In a particularly preferred method DNAs in accordance with the invention are injected into embryos, preferably at the single-cell stage. In some particularly preferred embodiments in this regard, DNA is injected in the pronucleus of a one-cell embryo. In other preferred embodiments in this regard, DNA is injected into the cytoplasm of a one cell embryo. In yet another particularly preferred embodiment in this regard, DNA is injected into an early stage, several cell embryo In these regards, in like manner, in yet other preferred embodiments a DNA-RNA hybrid is injected into an embryo, particularly single-cell embryos, into the pronucleus or the cytoplasm, or into an early stage embryo.

Somatic Cell Transgenesis

Similarly, in some aspects and embodiments in accordance with the present invention genetic elements and/or constructs for engendering gene expression to produce one or more desired polypeptide and/or proteins and/or other substances in saliva are introduced directly into an animal and incorporated into some of the animal's somatic cells, preferably cells of one or more salivary glands, particularly one or more salivary glands that are major(s) sites of saliva production, particularly cells, glands and animals in accordance with preferred embodiments of the invention set out elsewhere herein, especially, to reiterate a few of the preferred embodiments in this regard, one or more parotid glands that are major(s) sites of saliva production in monogastric ruminant animals that produce large quantities of saliva, especially ovine, caprine or bovine animals, particularly especially parotid glands of bovine animals.

In further preferred embodiments in this regard the genetic elements and/or gene constructs are introduced into salivary glands, preferably parotid glands, taken up by cells thereof, and, when integrated into the genome of the salivary gland cells, engender therein expression of a gene, and thereby the production of one or more desired substances in the saliva of the transgenic animals. Transgenic animals produced by such methods generally will be chimeric; i.e., transgenic only in some of their cells, i.e., salivary gland cells, not in others. Germ cells generally will not be altered—unless specifically targeted. The offspring of these animals thus generally will be normal; not transgenic. Despite this and other disadvantages, somatic cell mediated transgenic methods does offer a number of advantages, in principle. First, a seeming disadvantage of such methods—namely, lack of reproductive competence of the transgenic cells, which precludes inheritance in offspring of the transgene and its qualities—actually provides at least one important advantage. Since the transgene cannot be reproductively transmitted it is confined to the animals into which it is deliberately introduced, and somatic cell transgenesis thus provides a high intrinsic level of bio-containment. More practically, and perhaps more importantly, access to transgenic production through genetic manipulation of somatic cells does not involve the gestation and development periods usually required to obtain transgenic production using methods that rely on genetic engineering of eggs or embryos. This feature is particularly advantageous for animals that require months or years of gestation and development to reach the maturity required for transgenic production. Accordingly, somatic cell transgenesis also has the advantage that it be tried and assessed in relatively short time periods, and thereby can avoid uncertainty, lost time and long-term investments of resources that may attend the rather long wait before production can be tested in animals made by transgenesis using eggs or embryos. Furthermore, transgenesis via somatic cells can be carried out repeatedly on the same animal. Repetition can be sequential, which may be useful to repeat efforts to get a given experiment to work in a given animal, or to introduce a sequence of constructs into the same animal. Somatic transgenesis also allows the production of animals chimeric in several different ways at the same time. The same genetic alterations can be engendered in several specific tissues, glands or organs, for instance. Or different genetic manipulations can be carried out at different places in a single animal. Somatic cell transgenic methods can be used advantageously in all of these regards, and in other ways, in certain aspects and preferred embodiments of the invention herein disclosed.

Methods for genetic manipulation of salivary gland cells that can be useful in accordance with the present invention in these and other regards have been described, for instance, in Baum et al. (1999), *Critical Reviews in Oral Biology & Medicine* 10(3): 276-283, which is incorporated herein by reference in its entirely particularly in parts pertinent to transgenic expression of genes in salivary glands and production of desired substances in saliva, especially as to methods for somatic cell transgenesis in cells of salivary glands and/or those involved in producing saliva or components thereof and/or those useful for modifying saliva, particularly as to producing desired substances therein. Baum at al. review progress at that time in methods for transferring foreign genes to salivary gland cells in vivo. As described therein, there are a variety of well known and readily available replication-deficient recombinant adenovirus-derived vectors that can be used to transduce a cloned gene into salivary gland epithelial cell types and engender therein high level expression of the transgene, in rats. Gene transfer into salivary glands also has been achieved with non-recombinant adenoviruses, vectors derived from retroviruses, and with plasmid conjugates.

Purification of Constructs for Making Transgenic Animals

Constructs for producing one or more polypeptides and/or one or more proteins and/or one or more other substances of interest in saliva of transgenic non-human animals in accordance with the invention, such as double-stranded DNA and DNA:RNA hybrid constructs, can be prepared by any of a wide variety of well known molecular biology methods. DNAs in double-stranded form may be manipulated by conventional methods to provide constructs having the structures and properties set out elsewhere herein for expression in transgenic organisms, particularly cells of one or more salivary glands, especially one or more major glands of saliva formation, also especially one or more of the major glands for secretion of polypeptides and/or proteins and/or other substances of interest into saliva, also especially one or more major salivary glands that secrete the most polypeptide and/or protein into the saliva of the animal, also especially one or major salivary glands that secrete the greatest volume of saliva forming constituents in the salivary gland duct, particularly especially cells of the parotid glands of non-human monogastric ruminant mammals, preferably in this regard monogastric ruminant mammals that produce large volumes of saliva, also particularly especially porcine, ovine, caprine, bovine or equine mammals, very especially one or more parotid glands of bovine mammals.

For DNA:RNA hybrids, well known vectors that contain bacteriophage promoters, such as the T3 and T7 promoters can be used to produce RNA for DNA:RNA hybrids and well known vectors that produce single-stranded DNA may be used to produce single-stranded DNA for DNA:RNA hybrids.

Constructs can be amplified by conventional techniques for cloning and propagation in a host organism such as a bacterial host, a yeast host, an insect cell host, a mammalian cell host, or other suitable host. Constructs also can be amplified by in vitro methods such as PCR. Constructs can be derived from natural, cloned or synthesized DNA or RNA, in whole or in part. Polynucleotide constructs may contain modified bases as well as the bases that occur naturally in DNA and RNA.

Often constructs for making transgenic organisms in accordance with the invention are manipulated or propagated joined to or in the presence of other polynucleotides. These extraneous polynucleotides can be removed prior to using a construct to produce a transgenic organism. For instance, a genetic construct (such as an expression construct comprising (i) a structural gene for a polypeptide to be produced in saliva, operably linked to (ii) cis-acting regulatory and other signals sufficient for expression of the structural gene in salivary gland of the gland cells and secretion of the expressed polypeptide into the duct lumen, and into the saliva), that has been propagated and amplified as part of a cloning vector (such as a plasmid vector), generally can be released intact from the vector by restriction enzyme cleavage, then separated away from the vector restriction fragments by gel electrophoresis and then recovered from the gel, often by electroelution, all following standard molecular biology techniques. Similar techniques of gel electrophoresis and electroelution are useful to purify PCR amplicons as well. Constructs for introduction into cells to make transgenic organisms in accordance with the invention generally are purified by one or more steps, well known to those of skill in the art, such as, but not limited to HPLC, ultracentrifugation through a sucrose gradient, ultracentrifugation through an NaCl gradient or, in certain particularly preferred embodiments in this regard, by combination of two or more of electroelution, HPLC, sucrose gradient centrifugation and NaCl gradient centrifugation.

DNA Encoding Polypeptides

Genetic constructs that comprise one or more structural genes for one or more polypeptides and/or proteins of interest for use in making transgenic organisms in accordance with the invention can be obtained using standard molecular biology techniques, including but not limited to techniques for cloning, synthesizing and modifying DNAs, RNAs, PNAs and combinations thereof, among others. Genomic DNAs, minigenes and cDNAs are particularly preferred in this regard.

Structural gene-containing constructs, such as genomic DNAs, minigenes or cDNA constructs, encoding one or more polypeptides and/or one or more proteins derived from a variety of organisms may be used in the invention in this regard. For instance, genetic constructs encoding a polypeptide and/or protein that can be used for salivary gland cell-specific expression in accordance with the invention include, among others, those derived from genes and cDNAs of mammals, particularly murine, (mouse and rat), swine, ovine, caprine, bovine, equine animals, from primates and from humans. In this regard, among the most highly preferred DNAs are those derived from human genomic DNA and from human cDNAs.

Particularly preferred genetic constructs for use in the present invention are those that engender expression of human polypeptides and/or proteins of interest, particularly those polypeptides and/or proteins of preferred embodiments described elsewhere herein, particularly proteins that are (and/or a protein selected from the group consisting of) phytases, antibodies, growth hormones, and/or blood proteins including, but not limited to, serum albumin and proteins of hemostasis and/or thrombosis, especially in this regard fibrinogen, prothrombin, thrombin and von Willebrand Factor ("vWF"), and precursors thereof, very especially in this regard human fibrinogen, human prothrombin and human thrombin and precursors thereof. particularly among these human fibrinogen, human prothrombin, human thrombin and human vWF. Genomic DNAs, minigenes and cDNAs are preferred in some embodiments in this regard.

Genomic DNAs that encode a polypeptide and/or protein of interest can be obtained, for instance, from libraries of human genomic DNA or human cDNA. Clones encoding the polypeptide and/or protein of interest can be identified in the libraries by probe hybridization techniques. Probes specific to the target genomic clone or cDNA can be designed using well known and readily available software, based on a known gene sequence, or less desirably a polypeptide and/or protein sequence. Generally, partial or full sequences of previously characterized genomic or cDNA clones that can be used in this regard are available in well known and readily available databases of genomic and cDNA sequences, particularly for human genes, but also increasingly for genes of other organisms. Sequences for probes can be ascertained from the known sequences using off the shelf software designed for this purpose, which is available from commercial suppliers, as well as available over the world wide web. The probes then can be used to identify clones encoding the polypeptide and/or protein of interest in a cDNA or genomic DNA library using standard, well known library screening and cloning techniques.

Cloned genes for a variety of human blood proteins involved in maintaining hemostasis that can be used in this regard in accordance with the invention are set out in Degen (1992), *Seminars in Thrombosis and Hemostasis* 18(2): 230-242, which is incorporated herein by reference in its entirety particularly as to the foregoing in parts pertinent to genomic DNAs, minigenes DNAs and cDNAs encoding proteins involved in thrombosis and hemostasis. Genetic constructs that engender production of naturally occurring forms of preferred polypeptides and/or proteins of the invention are highly particularly preferred in some aspects and preferred embodiments of the invention. Genetic constructs that engender production of altered, mutated, and/or modified forms of the preferred polypeptides and/or proteins are preferred in other aspects and preferred embodiments of the invention.

Modifications can be introduced into naturally occurring forms of genes and of the polypeptides encoded thereby using techniques well known to the art, such as the synthesis of modified genes by ligation of overlapping oligonucleotides, and by introducing mutations directly into cloned genes, as by oligonucleotide mediated mutagenesis, inter alia.

Particularly preferred modifications in this context include but are not limited to those that alter post-translational processing as discussed above, that alter size, that fuse portions of other polypeptides and/or proteins to those of the polypeptide and/or protein of interest, that alter the active site of the polypeptide and/or protein of interest, that stabilize the polypeptide and/or protein of interest, that control transport and/or secretion of the polypeptide and/or protein of interest, that alter, augment, multiply, decrease or eliminate physiological activities of the polypeptide and/or protein of interest.

For instance, among modifications preferred in this regard are those that alter parts of a precursor of an active form of a polypeptide and/or protein of interest that do not alter the structure of the polypeptide and/or protein of interest derived from it, such as would be the case for activation of a polypeptide and/or protein of interest by proteolytic cleavage of an inactive precursor, such as, for example, activation of an inactive fusion protein by cleavage by Factor Xa complex. In this regard see, for instance, pages 514-516 in TEXTBOOK OF HEMATOLOGY, 2nd Edition, Shirlyn B. McKenzie, William & Wilkins, Baltimore (1996) which is herein incorporated herein by reference in parts pertinent to activation of inactive and other forms of precursors by proteolytic cleavage, particularly as to proteins of hemostasis and/or thrombosis that are synthesized as pro-bioactive polypeptides and/or proteins and subsequently converted to bioactive polypeptides and/or proteins, at least in part by proteolytic cleavage, including in this regard, but not limited to fibrinogen, prothrombin, thrombin and von Willebrand Factor ("vWF"), and precursors thereof, very especially in this regard human fibrinogen, human prothrombin and human thrombin and precursors thereof.

Further preferred embodiments in this regard relate to modifications that affect, alter, add to, or eliminate one or more of post-translational modifications of polypeptides of the invention. Certain particularly preferred embodiments in this regard relate to modifications that alter one or more physiological functions and provide improved characteristics and/or performance, such as improved activities, especially improved pharmacological and/or physiological activities, improved stability, improved properties for purification, and improved physiological persistence, among others.

In certain aspects of the invention in this regard, as set out above and in some details below, preferred embodiments of the invention in this regard relate to, among others, polypeptides and/or proteins that are (and/or are selected from the group consisting of) phytases, antibodies, growth hormones, and blood proteins including, but not limited to, serum albumin and proteins of hemostasis and/or thrombosis, especially in this regard fibrinogens, prothrombins, thrombins and von Willebrand Factors ("vWFs"), and precursors thereof, very especially in this regard human fibrinogen, human prothrombin and human thrombin, and precursors thereof.

Specifically as to certain embodiments of the invention relating to polypeptides and/or proteins that undergo γ-carboxylation, such as certain proteins involved in hemostatic process, preferred embodiments in this regard include modifications that result in one or more additions, deletions or alterations of sites of γ-carboxylation or to other sites that influence and/or modulate γ-carboxylation, and/or that change the γ-carboxylation of the thus modified polypeptides and/or proteins and thereby provide improved characteristics of the polypeptides and/or proteins of interest, specifically including but not limited to improved characteristics of calcium-dependent membrane binding, and/or to bind to and/or accrete at and/or localize to sites of injury, and/or improve the contribution of glutamic acid residues to modulating interaction and complex formation with other factors such as, for certain blood proteins in particular, vitamin K-dependent coagulation factors.

Certain preferred embodiments in this regard also relate to addition, deletion or alteration of sites to change glycosylation of polypeptides of the invention. Particularly preferred embodiments in this regard involve alterations to N-linked glycosylation sites, and sites that match the consensus sequence of N-linked glycosylation sites, such as Asn-X-Ser/Thr, the primary signature of N-linked glycosylation sites in human proteins, and other sites that match consensus and other signatures of sites of N-linked and other types of glycosylation in human and/or non-human proteins. Such sites are described, for instance, in Degen, *Seminars in Thrombosis and Hemostasis* 18(2): 230-242 (1992) which is incorporated herein by reference in its entirety, as to the foregoing particularly with regard to glycosylation sites and consensus glycosylation sequences in polypeptides and/or proteins of interest in accordance with the invention in this regard.

Particularly preferred embodiments in this regard include those that alter one or more glycosylation sites to provide one or more improvements in glycosylation-dependent activities of the altered polypeptides and/or proteins of interest, including but not limited to improved characteristics as to one or more of: one or more physiological activities, including but not limited to enzymatic activity, substrate preferences, binding to cofactors and other moieties, complex formation, thermal stability, resistance to proteases and physiological persistence, among other things. In this regard see, for instance, PROTHROMBIN AND OTHER VITAMIN K PROTEINS Vols I and II, Seegers and Walz, Eds., CRC Press, Boca Raton, Fla. (1986) which is incorporated herein by reference in its entirety, as to the foregoing particularly in parts pertinent to glycosylation of polypeptides and/or proteins in accordance with the invention, especially in this regard Vol. 1, Chapter 8, Kobata and Mizuochi, *Current Status of Carbohydrate Constituents and Prospects,* 81-94.

Polypeptides and Proteins

In an important aspect the invention provides polypeptides and/or proteins of interest, particularly in amounts and at costs that are advantageous for their production for commercial enterprise and/or that are commercially advantageous and/or that are economically viable, particularly in amounts and initially comprised in saliva and compositions derived from saliva from which they can be obtained in requisite purity and amount for use in veterinary and human health care applications, inter alia.

Polypeptides and/or proteins of preferred embodiments of the invention in these and other regards, include, among others: bioactive polypeptides and/or bioactive proteins (including single-chain and multi-chain bioactive proteins), and probioactive polypeptides and/or probioactive proteins (including single-chain and multi-chain probioactive proteins). In addition, certain polypeptides and/or proteins of particularly preferred aspects and embodiments of the invention in these and other regards include, among others, bioactive pharmaceutical polypeptides and/or bioactive pharmaceutical proteins (including single-chain and multi-chain bioactive pharmaceutical proteins), and probioactive pharmaceutical polypeptides and/or probioactive pharmaceutical proteins (including single-chain and multi-chain probioactive pharmaceutical proteins).

Among particularly preferred polypeptides and/or proteins, in accordance with the foregoing aspects of the invention are (and/or are selected from the group consisting of) phytases, antibodies, growth hormones, and blood proteins including, but not limited to, serum albumin and proteins of hemostasis, especially in this regard fibrinogen, prothrombin, thrombin and von Willebrand Factor ("vWF"), very especially in this regard human serum albumin, human fibrinogen, human prothrombin, human thrombin and human vWF.

In all the foregoing regards, among especially preferred polypeptides and/or proteins and/or other substances are transgenic polypeptides and/or proteins and/or other substances produced in transgenic organisms in accordance with the invention herein disclosed, particularly in transgenic saliva, wherein the transgenic polypeptides and/or proteins and/or other substances thus produced differ from the naturally occurring polypeptides and/or proteins and/or other substances in one or more detectable characteristics. In preferred embodiments in this regard the one the transgenicly produced polypeptide and/or protein or other substance from the naturally occurring polypeptide and/or protein or other substance in one or more structural characteristics. In especially preferred embodiments in this regard the transgenic and naturally occurring polypeptide and/or protein or other substance differ in their covalent structure and/or in activity. Structural characteristics that differ in certain preferred embodiments in this regard, include but are not limited to structural features produced by proteolytic cleavage and/or processing, and post-translational covalent modifications including but not limited to glycosylation, acetylation, gamma-carboxylation, methylation, sulfation, and/or poly-ADP-ribosylation, among others.

In another aspect in these regards, the invention provides in certain of its preferred embodiments transgenic polypeptides and/or proteins in accordance with the foregoing that differ in primary amino acid sequence from that of the naturally occurring non-transgenic polypeptide and/or protein. In further preferred embodiments in this regard the polypeptide and/or protein differs from the non-transgenic, naturally occurring polypeptide and/or protein in primary structure and in structures produced by post-translational processing and/or modification. In yet other preferred embodiments in this regard the transgenic substances have substantially the same or the same activities as the non-transgenic substances, but in other preferred embodiments in this regard the transgenic substances differ from the non-transgenic substances in one or more of their activities and/or their specific activities.

In yet additional aspects in this regard, the invention provides in certain particularly preferred embodiments non-naturally occurring substances produced by a transgenic animal in accordance with the foregoing and as described elsewhere herein, wherein the transgenic polypeptide and/or protein or other substance differs from that occurring in nature in its complexation with itself or with other substances and/or it comprises a moiety not present in the substance as it occurs in nature and/or wherein the substance, polypeptides and/or proteins does not comprise a moiety present in the substance as it occurs in nature In yet further aspects in this regard, the invention provides in certain particularly preferred embodiments non-naturally occurring substances produced by a transgenic animal in accordance with the foregoing and as described elsewhere herein, wherein the transgenic polypeptide and/or protein differs from that occurring in nature in its primary structure and wherein its amino acid sequence differs from the amino acid sequence of the polypeptide and/or protein as it occurs in non-transgenic animals but otherwise has 80% to 90%, preferably 90% to 95%, and more preferably 95% to 98%, identity with the amino acid sequence of the polypeptide and/or protein as it occurs in the non-transgenic animal.

Preferred embodiments of the invention in this regard in particular provide polypeptides and/or proteins that are homologous to human proteins that are (and/or are selected from the group consisting of) human antibodies, human growth hormones, and human blood proteins including, but not limited to, human serum albumin and human proteins of hemostasis, especially in this regard human fibrinogen, human prothrombin, human thrombin and human von Willebrand Factor ("vWF"), very especially in this regard human serum albumin, human fibrinogen, human prothrombin, human thrombin and human vWF, including especially probioactive and bioactive polypeptides and/or proteins in this regard. Particularly preferred polypeptides in this regard comprise a region that is 70% or more, especially 80% or more, more especially 90% or more, yet more especially 95% or more, particularly 97% or more, more particularly 98% or more, yet more particularly 99% or more identical in amino acid sequence to the amino acid sequence of the corresponding naturally occurring human proteins or other polypeptide, and that retain the desirable activities and other characteristics of the polypeptide and/or protein.

Identity in this regard can be determined using a variety of well known and readily available amino acid sequence analysis software. Preferred software includes those that implement the Smith-Waterman algorithm, considered a satisfactory solution to the problem of searching and aligning sequences. Other algorithms also may be employed, particularly where speed is an important consideration. Commonly employed programs for alignment and homology searching, and for calculating identities of DNAs, RNAs and polypeptides that can be used in this regard include FASTA, TFASTA, BLASTN, BLASTP, BLASTX, TBLASTN, PROSRCH, BLAZE and MPSRCH, the latter being an implementation of the Smith-Waterman algorithm for execution on massively parallel processors made by MasPar.

The BLASTN, BLASTX and BLASTP programs are among preferred programs for homology and identity determinations, the former for polynucleotide sequence comparisons and the latter two for polypeptide sequence comparisons—BLASTX for comparison of the polypeptide sequences from all three reading frames of polynucleotide sequence and BLASTP for a single polypeptide sequence. BLAST programs provide several user definable parameters that are set before implementing a comparison, including the following. (1) A value is set for E to establish the number of High Scoring Segment Pairs expected by chance. (2) A value is set for S to establish the cut-off score for reporting a High Scoring Segment Pair, i.e., for listing a segment pair as a significant match. Usually S is calculated from E. The values of E and S calculated for a given search string will be different on different databases. Accordingly, the values chosen for E and for the S cut off often are different for different databases. To normalize between different databases a parameter called Z is used. While the use of sophisticated techniques for setting E and S are entirely consistent with the present invention, a presently preferred method for determining similarity, homology and identity of sequences using BLAST is to set S to the default value (10) and to calculate E from the default value of S using the default setting in the BLAST program being employed.

Identity and homology determining methods are' discussed in, for instance, GUIDE TO HUMAN GENOME COMPUTING, Ed. Martin J. Bishop, Academic Press, Harcourt Brace & Company Publishers, New York (1994), which is incorporated herein by reference in its entirety with regard to the foregoing particularly in parts pertinent determining identity and or homology of amino acid or polynucleotide sequences, especially Chapter 7. The BLAST programs are described in Altschul et al., "Basic Local Alignment Research Tool", *J Mol Biol* 215: 403-410 (1990), which is incorporated by reference herein in its entirety particularly regarding the determination of similarity, homology and/or identity of DNA, RNA and/or protein sequences in accordance with the present invention. Additional information concerning sequence analysis and homology and identity determinations are provided in, among many other references well known and readily available to those skilled in the art: NUCLEIC ACID AND PROTEIN SEQUENCE ANALYSIS: A PRACTICAL APPROACH, Eds. M. J. Bishop and C. J. Rawings, IRL Press, Oxford, UK (1987); PROTEIN STRUCTURE: A PRACTICAL APPROACH, Ed., T. E. Creighton, IRL Press, Oxford, UK (1989); Doolittle, R. F.: "Searching through sequence databases" *Met Enz* 183: 99-110 (1990); Meyers and Miller: "Optimal alignments in linear space" *Comput Applica in Biosci* 4: 11-17 (1988); Needleman and Wunsch: "A general method applicable to the search for similarities in amino acid sequence of two proteins" *J Mol Biol* 48: 443-453 (1970) and Smith and Waterman "Identification of common molecular subsequences" *J Mol Biol* 147: 1950 et seq. (1981), each of which is incorporated herein by reference in its entirety with reference to the foregoing particularly in parts pertinent to sequence comparison and identity and homology determinations.

Among preferred embodiments in this regard are those wherein further the polypeptide and/or protein has one or more activities of the polypeptide and/or protein as it occurs naturally in the non-transgenic animal, those wherein the polypeptide and/or protein has one or more activities with substantially the same or the same specific activity as the specific activity of the polypeptide and/or protein as it occurs in the non-transgenic animal, and those wherein one or more activities are substantially different in a desired way, either less or more, than those of the non-transgenic polypeptides and/or proteins. Particularly preferred embodiments in all these regards include those in which one or more of the aforementioned activities is a physiological activity, those in which one or more activities are an enzymatic activity, a binding activity, an intra-cellular transport activity, those in which one or more activities are physiological persistence and/or half life, and those in which one or more activities are pharmacological activities, particularly pharmacological activities effective for treating one or more disorders or diseases in a plant, animal or human patient.

In further aspects in this regard, in accordance with the foregoing, the invention provides in certain further particularly preferred embodiments non-naturally occurring polypeptides and/or proteins, wherein the transgenic polypeptide and/or protein differs in its specific activity from that of the naturally occurring polypeptides and/or proteins, wherein in certain especially preferred embodiments in this regard the specific activity is (and/or is selected from the group consisting of) 25% to 95%, 50% to 95%, 75% to 95%, 80% to 97%, 85% to 98%, 90% to 105%, 75% to 125%, 50% to 110%, 90% to 110%, about 100%, 100%, or more than 110% of the specific activity of the naturally occurring protein in its highly active and highly purified form. Relative specific activities in this regard generally will be determined by using an accepted and acceptable reference preparation that can serve as an accurate calibration standard for specific activities determination, as described in somewhat greater detail elsewhere herein.

In yet additional aspects in this regard, the invention provides in certain of its preferred embodiments probioactive proteins and/or probioactive polypeptides that, as to one or more bio-activities are inactive in the "probioactive" form; but, when activated have desired activities in the desired degree, especially in many cases those that are quite inactive in the probioactive form and when activated provide a high degree of one or more bioactivities, especially a high degree of specific activity, particularly especially the specific activity of the native protein, or a specific activity approaching the theoretical maximum specific activity. Assessing the activities of polypeptides and/or proteins in this regard generally is done using methods appropriate to the polypeptide and/or protein and to the activity or the activities being measured. Such methods generally will be those developed to measure the properties and/or activities of naturally-occurring polypeptides and/or proteins, and of variants thereof produced by in vitro mutagenesis, inter alia. As to each polypeptide and/or protein property and/or activity, such techniques and protocols, suitable for use with a given polypeptide and/or protein of the present invention, will be well know and readily available to those skilled in the pertinent arts.

Especially preferred in this regard are bioactivities of preferred polypeptides and/or proteins of the invention including bioactivities of (and/or are selected from the group consisting of) phytases, antibodies, growth hormones, and blood proteins including, but not limited to, serum albumin and proteins of hemostasis, especially in this regard fibrinogen, prothrombin, thrombin and von Willebrand Factor ("vWF"), very especially in this regard human serum albumin, human fibrinogen, human prothrombin, human thrombin and human vWF.

In this regard especially preferred embodiments are those that have a desired degree of one or more of the activities, especially one or more of the bioactivities of the polypeptide and/or protein, especially one or more of the bioactivities of the polypeptide and/or protein of interest as it occurs when isolated from a non-transgenic organism in which it naturally occurs; i.e., its naturally occurring activity or activities, especially when measured by reference to a preparation of the polypeptide and/or protein that is considered to be homogeneous and highly active, particularly especially a high specific activity reference standard preparation of the polypeptide and/or protein purified to a high degree of homogeneity, very especially a reference standard preparation of the polypeptide and/or protein that is considered to be a homogeneous, fully active preparation of the polypeptide and/or protein, most especially as to human polypeptides and/or proteins, an accepted standard reference preparation, especially one considered to be a homogeneous, fully active preparation of the naturally occurring human polypeptide and/or protein. It will be appreciated that such highly purified and active preparations may not be available, in which case a well-accepted standard is preferred in the invention in this regard. It also will be appreciated that, for polypeptides and/or proteins that have not been prepared in highly purified, highly active form, inter alia, transgenic polypeptides and/or proteins of the present invention may, in one or more specific activities, exceed the specific activities of existing reference preparations of the naturally occurring polypeptide and/or protein. Accordingly, in some aspects and embodiments of the invention in this regard, preferred proteins and/pr polypeptides of the present invention may exceed in their degree one or more activities and/or specific activities of available and/or known preparations of the naturally occurring, non-transgenic polypeptide and/or protein.

In all of the foregoing regards, as to activities, especially bioactivities, particularly preferred embodiments of the invention have 50% or more of one or more of the activities and/or specific activities of a reference standard preparation of the polypeptide and/or protein, 65% or more is particularly highly preferred in this regard, 75% or more is especially highly preferred, 85% particularly especially highly preferred, 90% or more very particularly especially highly preferred, and 95% or more is especially very particularly especially highly preferred. Other preferred embodiments in this regard have 25% to 175% of one or more of the activities and/or specific activities of a reference standard preparation, particularly 50% to 150%, especially 75% to 125%, also especially 85% to 115%, particularly especially 90% to 110%.

Among preferred embodiments in this regard are derivatives that differ in post-translational modification from that found in the human polypeptide and/or protein prepared from natural sources. Especially preferred in this regard are differences that do not cause contraindications when administered to animal or human patients. Also among particularly preferred embodiments in this regard are derivatives that have a lower or a higher content or different pattern of various particular post-translational modifications exhibited by the proteins and/or polypeptide from a naturally occurring source, particularly a human polypeptide and/or protein, especially those differences that do not cause contraindication when administered to animal or human patients and/or that have improved qualities as to one or more end uses.

For instance, as to certain vitamin K dependent proteins important to the processes of human hemostasis, γ-carboxylation that differs detectably from the γ-carboxylation that occurs in the protein isolated and purified from human subjects is preferred, particularly distinguishably different γ-carboxylation in transgenic polypeptides and/or proteins that otherwise are considered by the FDA and/or other drug approval authorities to be clinically acceptable and/or equivalent and/or superior in one or more characteristics to that of the naturally occurring protein. In other preferred embodiments in this regard, much the same is the case for other post-translational modifications, including those set out above, alone or in combination, including but not limited to glycosylation (particularly in some instances in this regard fucose content and/or N-acetylgalactosamine content), amidation, acetylation, methylation, and lipidation.

Harvesting Saliva

A variety of methods are available for collection saliva of genetically engineered animals in accordance with various aspects and embodiments of the present invention. Among these are several methods for saliva collection depending on the relative amounts to be collected. For example, if small amounts of saliva are required for initial analyses of the presence of the transgene product, then collection methods suitable for small amounts but not large amounts can be used. For collecting small volumes, saliva can be absorbed from the buccal cavity by sponge absorption and then recovered from the sponge. Alternatively, small to intermediate amounts of saliva can be collected from the buccal cavity by aspiration. If copious quantities of saliva are desired, other methods should be used. Preferably, in some aspects and preferred embodiments of the invention large volumes of saliva are collected directly from salivary gland ducts, preferably parotid gland ducts. In preferred embodiments of the invention in this regard, saliva is collected through flexible tubing from a cannula placed in the duct by surgical procedures. In brief, the surgery involves making an incision near the lower jaw, isolating and exposing the parotid duct, and cannulating the duct using flexible tubing. The tubing is secured surgically, so that it remains in place in the duct. The opposing end of the cannula is externalized through the skin adjacent to the initial incision. The externalized cannula then is affixed to a collection device, for constant collection of salivary fluids. The cannula and collection device in preferred embodiments are self-contained and are secured solely to the animal, generally to the neck, ensuring as much as possible that they do not constrain the animal's movements or cause it other discomfort that might cause it to accidently dislodge the collection reservoir or other parts of the apparatus, and perhaps cause its accidental removal. Saliva can be collected in these and other ways not presented here suitable for use in various aspects of the invention. The methods and devices reviewed briefly below are further illustrative in this regard, and augment the foregoing as to methods that can be used for collecting saliva in accordance with the invention herein disclosed.

Phillips and co-workers described a method and a device that can be used for collecting saliva in accordance with the present invention from dog parotid glands. See in this regard Phillips at al. (1983), *Laboratory Animal Science* 33(5): 465-466, which is incorporated herein by reference in its entirety as to methods and devices for collecting saliva. Lindner and co-workers described another method suitable for use in the invention in this regard, particularly for collecting saliva of exercising animals, which they used to collect saliva from horses. See in this regard Lindner et al. (2000), *J Equine Vet*

Sci 20(1): 52-54, which is incorporated herein by reference in its entirety as to methods and devices for collecting saliva. Gunzel and Hoppe described a method for collecting saliva suitable for use in some aspects of the present invention using a surgical technique for preparing permanent esophageal fistulas, which they used to collect saliva from ovine. See in this regard Gunzel and Hoppe (1976), *DTW-Dtsch-Tierarztl-Wochenschr* 83(9): 407-408, which is incorporated herein by reference in its entirety as to methods and devices for collecting saliva. Sahlu and co-workers described a method for collecting saliva by cannulating salivary glands that can be used in accordance with aspects of the invention herein described, which they used to collect saliva from caprine parotid glands. See in this regard Sahlu et al. (1992), *Canadian Journal of Animal Science* 72(2): 245-252, which is incorporated herein by reference in its entirety as to methods and devices for collecting saliva. Fell and Shutt described methods for collecting saliva suitable for use in accordance with various aspects of the invention, which they used to collect saliva from sheep and calves. See Fell and Short (1986), *Proceedings of the Australian Society of Animal Production* 16: 203-206, which is incorporated herein by reference in its entirety as to methods and devices for collecting saliva. Beal also described methods for collecting saliva, and methods for measuring saliva flow, suitable for use in accordance with various aspects of the present invention, which was used to collect saliva from ewes by parotid gland cannulation. See in this regard Beal (1977), *Journal-of-Physiology* 267(1): 19P-20P, which is incorporated herein by reference in its entirety as to methods and devices for collecting saliva. Lutz and co-workers described techniques for collecting saliva from awake, unrestrained, adult animals suitable for use in various aspects of the present invention, which they used to collect saliva from monkeys to measure cortisol levels. See in this regard Lutz et al. (2000), *American Journal of Primatology* 52(2): 93-99, which is incorporated herein by reference in its entirety as to methods and devices for collecting saliva.

Purifying Proteins, Polypeptides and/or Other Products from Saliva

A wide variety of well known techniques may be employed to isolate and purify polypeptides and/or proteins from transgenic saliva in accordance with the present invention. In general, standard methods for preparing compositions from saliva and/or for isolating, purifying and preparing polypeptides and/or proteins can be used in this regard, including but not limited to methods used to purify polypeptides and/or proteins from natural sources, from host cells used for their production via cell-engineering, recombinant DNA techniques, cell culture, and transgenic production methods, including methods for obtaining polypeptide and/or proteins from milk of transgenic animals. Among preferred general purification methods in this regard are those that do not adversely affect yield or activity. In some aspects of the invention it is preferred that polypeptides and/or proteins are isolated from the saliva as soon as possible after it is obtained from the transgenic mammal. Particularly preferred for obtaining polypeptides and/or proteins from saliva in accordance with the present invention are methods involving cryoprecipitation, ion-induced precipitation, anion exchange, and/or immunochromatography. Among such methods are methods used to isolate proteins from transgenic milk that may also be adopted to isolate polypeptides and/or proteins from transgenic saliva in accordance with the invention herein disclosed. By way of illustration in this regard, such methods are described and variously exemplified in, among others: Denman et al. (1991): *Transgenic expression of a variant of human tissue-type plasminogen activator in goat milk. II: Purification and characterization of the recombinant enzyme, Bio/Technology* 9: 839-843 and Wright et al. (1991): *High level expression of active human alpha-9-anti-trypsin in the milk of transgenic sheep, Bio/Technology* 9: 830-834, which are incorporated herein by reference in their entirety particularly in parts pertinent to purification of proteins from transgenic animals.

Some constituents of saliva, such as proteases, may degrade or be otherwise deleterious to transgenic proteins. Methods for producing proteins and other substances in saliva may have to anticipate and prevent deleterious effects of this type. Among preferred methods in this regard are rapid processing of saliva, the use of low temperatures that inhibit protease activity and or decrease degradation of transgene products in saliva, and the use of protease inhibitors and/or inhibitors of other substances that may be present in saliva that deleteriously affect polypeptides and/or proteins and/or other substances of interest produced therein in transgenic animals in accordance with the invention herein described. Specific inhibitors that may be useful in this regard are well known to those of skill, and are widely available from commercial reagent suppliers such as Sigma Chemical Company. Similarly useful in this regard are stabilizers that may be employed to improve the yield of substances from transgenic saliva produced in accordance with the invention.

Yields and Properties of Proteins Produced from Saliva

In preferred embodiments of the invention methods are used for isolation and purification of polypeptides and/or proteins that provide a high yield of intact, active protein. Particularly, preferred embodiments of the invention in this regard include those that provide preparations that have a high percentage of protein having the aforementioned one or more activities, especially bioactivities, particularly those with preferred degrees of specific activities, as recited elsewhere herein.

In preferred embodiments of the invention in this regard, the methods provide polypeptides and/or proteins in satisfactory, desired yield, purity and quality, and at cost sufficiently low for commercially advantageous and/or economically viable transgenic production. Methods of particularly preferred embodiments of the invention in this regard provide yields that are better than those previously achieved by other methods, either as to concentration, total amount of polypeptide and/or protein obtained, activity, and/or specific activity and/or homogeneity, including homogeneity of activity, and/or specific activity, physiological activity, general or specific post-translational modification, including but not limited to γ-carboxylation and glycosylation, as appropriate for a given polypeptide and/or protein, a combination of one or more of any of the foregoing, proteolytic processing and/or activation, among others.

Saliva of transgenic non-human mammals in preferred embodiments of the invention in this regard have yields of the pure polypeptide and/or protein in the range of 1 ng/ml to 5 mg/ml, and in some cases more than that.

Activation of Proteins Produced in Precursor Form

In some preferred embodiments of the invention transgenic proteins and/or polypeptides are produced in transgenic organisms in an inactive form (referred to herein as a "proactive" form and/or, as to biological activity, "a probioactive" form) to an active form (referred to herein as an "active" form and/or, as to biological activity, a "bioactive" form).

Activation in this regard preferably is carried out in accordance with this aspect of the invention after isolation of the transgenic polypeptide and/or protein from the organism. It may be carried out at any stage of purification thereafter, including at any time from immediate isolation to the point of end-use requiring the activity in question of the transgenic polypeptide and/or protein in its active form.

One method of activation in this regard involves proteolytic cleavage of the proactive form of the polypeptides and/or proteins. The cleavage site for activation in such methods may be one or more naturally occurring sites for activation in the polypeptides and/or proteins, or it may be one or more different sites, such as sites introduced for this purpose or sites utilized by cleavage agents that do not ordinarily act on the polypeptide and/or protein. If cleavage at more than one site is involved, the agents for cleavage at each site may be the same or may be different, and the different sites may be cleaved in a single reaction or in two or more successive reactions that occur and/or can be controlled and/or can be carried out independently of one another. Such cleavage may be carried out using one or more proteolytic enzymes, including those that naturally cleave the polypeptide and/or protein during physiological processes and/or those that do not ordinarily cleave the polypeptide and/or protein, including those that have been engineered into the transgenic product. Activation by cleavage also may be accomplished by chemical methods, among others.

Among preferred enzymatic activation methods are those that use Factor Xa. Useful methods in this regard are described in, among others, Rosing et al., *J. Biol. Chem.* 261(9): 4224-4228 (1986); Krishnaswamy et al., *J. Biol. Chem.* 261(19): 8977-8984 (1986); Boscovic et al., *J. Biol. Chem.* 265(18): 10497-1010505 (1990); Tans et al., *J. Biol. Chem.* 266(32): 21864-2873 (1991); Tijburg et al., *J. Biol. Chem.* 266(6): 4017-4022 (1991; and Walker et al., *J. Biol. Chem.* 269(44): 27441-227450 (1994) each of which is incorporated herein by reference in its entirety in parts pertinent to activation of proactive polypeptides and/or proteins by Factor Xa cleavage.

Also among preferred enzymatic activation methods in this regard are those that use venom proteases. Methods useful in this regard are described in, among others, Franza et al., *J. Biol. Chem.* 250(7): 7057-7068 (1965) and Rhee et al., *Biochemistry* 21: 3437-3443 (1982) each of which is incorporated herein by reference in its entirety in parts pertinent to activation of transgenic proteins and/or polypeptides by cleavage with venoms.

Further among preferred enzymatic activation methods are those that utilize endogenous enzymes, such as activating enzymes that occur in saliva.

Chemical methods that can be used for activation in accordance with some aspects and embodiments of the present invention in this regard are preferred for large scale preparations; although, enzymatic methods also may be used for large scale processes (and chemical methods can be used for small preparations). Among highly particularly preferred chemical activation methods useful in certain particular aspects and embodiments of the invention are sodium citrate activation methods. Methods for sodium citrate activation useful in this regard are described in, among others, Seegers et al., *Blood* 5: 421-433 (1950), Heldebrandt et al., *J. Biol. Chem.* 248(10): 3642-3652 (1973) and PROTHROMBIN AND OTHER PROTEINS Vols I and II, Seegers and Walz, Eds., CRC Press, Boca Raton, Fla. (1986) especially in this regard Vol. I, Chapter 9, Seegers, *Prothrombin and Factor X Activation in 25% Sodium Citrate Solution and Related Phenomena,* 95-101, each of which is incorporated herein by reference in its entirety in parts pertinent to activation of transgenic proteins and/or polypeptides in accordance with this aspect of the invention. Another chemical activation method useful in this regard in certain aspects and preferred embodiments of the invention is activation using protamine, particularly protamine sulfate. Protamine activation methods useful in this regard are described in Miller, *Ann. N.Y. Acad. Sci.* 370 336-342 (1981) which is incorporated herein by reference in its entirety in parts pertinent to activation of proactive polypeptides and/or proteins by protamines. Yet another preferred chemical activation method useful in this regard is activation using polylysine. Polylysine activation methods useful in this regard are described in Miller, *J. Biol. Chem.* 236: 63-64 (1960) which is incorporated herein by reference in its entirety in parts pertinent to activation of transgenic polypeptides and/or proteins by polylysine in accordance with this aspect of the invention.

Activity Assays

Characteristic activities of many polypeptides and/or proteins and/or other substances produced in transgenic saliva in accordance with the present invention generally can be measured by one or more standard assays routinely employed for the purposes and well known to those of skill in the art. In general, any assay known to the art for detecting and/or characterizing and/or measuring quantitatively an activity of a polypeptide and/or protein and/or other substance (such as a naturally occurring, recombinantly produced, or transgenicly produced polypeptide and/or protein) can be used for detecting and/or characterizing and/or measuring quantitatively the same (or a sufficiently similar) activity of the same (or sufficiently similar) polypeptide and/or protein and/or other substance produced in saliva of a transgenic animal in accordance with the present invention. Among assays of activities useful in this regard, particularly as to certain aspects and preferred embodiments of the invention relating to, inter alia, preferred polypeptides and/or proteins set out elsewhere herein are: ligand binding assays, protein interaction assays, membrane binding assays, chromogenic, fluorimetric, and radiometric enzyme activity assays, including co-factor dependent, ligand-dependent and/or membrane-dependent enzyme assays.

For instance, standard assays routinely employed in research, clinical laboratories and manufacturing quality control procedures for detecting and/or characterizing and/or measuring activities of blood proteins in research, patient and manufacturing process samples can be used as well to detect and/or characterize and/or measure quantitatively the same activities of blood proteins produced in transgenic saliva. Thus, for example, the standard APTT assay, ELISA assay and chromogenic assay of amidolytic activity used to measure amidolytic activities of prothrombin and thrombin in research and clinical laboratories also can be used to determine amidolytic activities of prothrombin and thrombin produced in and purified from transgenic saliva.

For quantitative determinations of activity, preferably, a reference standard preparation is used to accurately quantify amounts and activities. Standard preparations suitable to this purpose often are available, particularly for clinically significant substances. Thus, generally, suitable standards are available for proteins of clinical relevance, such as, thrombin, prothrombin and fibrinogen. Standards used by clinical laboratories, such as those from commercial suppliers of clinical laboratory reagents of this type, are suitable in this regard. A preferred source of reference standard preparations, when available, is the NIH, the WHO, the ATCC, other non-commercial recognized standards-setting organizations, and commercial venders of standard preparations established by such organizations and/or standard preparations calibrated by comparison to the established standard preparations.

For instance, amidolytic activity of prothrombin in a sample can be determined using a chromogenic substrate and colorimetric assay routinely employed in clinical diagnostic laboratories, as described in U.S. Pat. No. 5,811,279, which is incorporated by reference herein in its entirety in parts pertinent to assay of prothrombin and thrombin activities. In brief, in accordance with the standard clinical laboratory procedure, amidolytic activity of the prothrombin sample is determined as follows. Prothrombin is converted to thrombin, and amidolytic activity thus activated, by incubating the prothrombin sample at 25° C. with Factor X at a concentration of 120.5 mµg/ml Factor X in 1 mM EDTA and PEG 4,000, pH 7.4. Amidolytic activity then is determined by incubating the activated sample with S-2238 (a chromogenic substrate for amidolytic activity). The amount of color generated in the assay indicates the amount of amidolytic activity in the sample. For quantitative estimations, serial dilutions of each sample generally are performed alongside serial dilutions of a well characterized reference preparation of known prothrombin concentration and activity, preferably a reference preparation calibrated relative to an accepted National or International Standard reference preparation, so that the amount of activity in the transgenic product can be expressed in standard relative units and specific activity.

Clotting assays also may be used to characterize the activities of clotting-related proteins and/or polypeptides produced in transgenic saliva in accordance with the present invention, such as prothrombin and/or thrombin. Clotting activity can be measured by a variety of conventional methods, such as described in U.S. Pat. No. 5,445,958, which is incorporated herein by reference in its entirety in parts relating to measuring the activities of thrombin and prothrombin in this and other respects. Unitage of the clotting activity determined by such assays preferably is defined in terms of a Working Standard, such as, for illustrative example, Working Standard 87/532, calibrated against the 1st International Standard for Factors. Use of accepted calibrated standards advantageously allows comparison of different assays to one another.

The amounts of polypeptides and/or proteins of the present invention can be measured by a variety of well known methods that are routinely used for the purpose by those of skill in the pertinent arts, many of which employ antibodies or antibody-derived or other immuno-reagents that are useful antigen-determining reagents, i.e., reagents that bind with sufficient specificity and avidity to discriminate by their binding the target antigen from other constituents in a sample. Analytical techniques of this type for measuring the amount of a polypeptide and/or protein of the invention can be carried out in solution, by solid phase ELISA, using gel electrophoresis, by Western blotting, by methods that utilize HPLC and by a variety of other methods using one or more of many other commonly employed separation techniques. Such techniques are well known and routinely employed by those of skill in the art, who will understand their advantageous applications to determinations useful in the present invention.

Many methods for measuring and characterizing transgenic products in accordance with the invention herein disclosed will employ well characterized preparations of the product as reference standards of mass, concentration, size, structure and/or activity. Methods for making appropriate reference preparations for this purpose generally are specific to the particular product of interest; but, a variety of such techniques generally are well known for each transgenic product and, for many of the polypeptides and/or proteins, as well as other products, highly purified and well characterized standards are available from commercial sources and/or non-profit research organizations and, in many cases, recognized standards setting organizations.

For instance, human prothrombin (Factor II) prepared from fresh frozen human plasma is available in 20 mM Tris-HCl/0.1 M NaCl/1 mM Benzamidine/pH 7.4 as a homogeneous preparation (as judged by 10% SDS-PAGE gels) that shows no reduction upon incubation with 2-mercaptoethanol, having an Extinction Coefficient (1%) of 13.6, a specific activity of 1 unit/90 µg, and a molecular weight of 72,000 daltons. As another example, human thrombin (Factor IIa) prepared from homogeneous human prothrombin by activation with Factor Xa, Factor Va, and phospholipid is available as a homogeneous preparation (as judged by 10% SDS-PAGE gel electrophoresis) with a minimum activity of 2,700 NIH units/mg compared to NIH standard reference preparation of the protein. The preparation is supplied in 50 mM Sodium Citrate/0.2 M NaCl/0.1% PEG-8000/pH 6.5, with an Extinction Coefficient (1%) of 18.3, and a molecular weight of 37,000 daltons. A variety of other reagents and standards useful for determining the amounts and activities of this protein are well known and widely available as well.

Illustrative Uses of Proteins Produced Transgenicly from Saliva

The transgenic animals, compositions and substances, inter alfa, produced by and in accordance with the invention have many uses, including the production of proteins—and the transgenic proteins thus produced—including both clinical and non-clinical applications. Among preferred uses in this regard are clinical and veterinary uses, particularly as to certain polypeptides and/or proteins of preferred embodiments of the inventions set out above. Among clinically important preferred applications in this regard are uses of certain preferred polypeptides and/or proteins of the invention, particularly prothrombin and thrombin, and fibrinogen to promote hemostasis, to improve anastomoses, to control hemorrhage, to achieve good hemostasis on bone defects, to seal vascular prostheses, to seal lesions and stumps, to treat pleurodesis, to close fistulas, to seal membranes, in procedures to extract stones and to prevent or reduce perioperative bleeding, to mention just a few. Additional uses in this regard are set out, for instance, in PROTHROMBIN AND OTHER VITAMIN K PROTEINS Vols I and II, Seegers and Walz, Eds., CRC Press, Boca Raton, Fla. (1986) which is incorporated herein by reference in its entirety, as to the foregoing particularly in parts pertinent to uses of prothrombin, thrombin and fibrinogen, especially in this regard Vol. II, Chapter 7, Deutsch, *The Clinical Use of Thrombin,* 92-103.

Particularly preferred embodiments in this regard especially relate to uses to promote hemostasis per se. Among a wide variety of such uses preferred embodiments relate to using transgenic saliva-produced probioactive thrombin (e.g., prothrombin) and/or bioactive thrombin and/or probioactive fibrinogen and/or bioactive active fibrinogen (and/or related proteins) in accordance with the invention to promote hemostasis in animals and/or humans, particularly at, to name just a few types of sites and wounds, lacerations and other wounds, sites of organ rupture, sites of bleeding during surgery, burn sites, sites of traumatic injury, surgical sites such as partial resections, including partial brain resections, bleeding biopsies, sites of tumor extirpation, including tumors from parenchymatous organs such as liver, spleen, pancreas, kidney, braih and prostate gland among others, sites of donations of skin grafts, sites of skin grafts, extraction of teeth sites, nose bleeding, sinus bleeding, bleeding in or near bones, gastrointestinal bleeding, and conjunctival wounds.

In this regard, preferred embodiments relate to uses of polypeptides and/or proteins of the invention, particularly prothrombin and thrombin, to promote anastomoses, particularly and to, among other things, tighten classically sutured anastomoses, to reduce the number of sutures in, for example, anastomoses of intestines, small vessels, maxillo-facial vessels and extracranial anastomoses, to prevent kinking of arterial grafts, and to promote the combination of nerve endings, to name but a few.

In this regard further preferred embodiments relate to uses of polypeptides and/or of the invention, such as fibrinogen in particular, produced from transgenic saliva to promote hemostasis in surgery and wounds associated with trauma, particularly wounds in civilian and military personnel that result from warfare. Particularly highly preferred embodiments in this regard relate to uses of polypeptides and/or proteins of the invention produced transgenicly from saliva, particularly fibrinogen, especially human fibrinogen, including as well fibrinogen-related polypeptides and/or proteins, including among others: muteins, mini-proteins, truncated polypeptides and/or proteins, hybrid proteins, fusion polypeptides, and the like, such as these and other fibrinogen-related polypeptides and/or proteins derived from a fibrinogen or a gene encoding a fibrinogen by such methods as in vitro mutagenesis, cloning and recombination, enzymatic or chemical cleavage and/or modification and the like. Fibrinogen-related polypeptides and/or proteins in this regard have, in pertinent parts, a high degree of amino acid sequence homology and/or DNA sequence identity to a fibrinogen or a gene for a fibrinogen, respectively, and that have characteristics and functions of fibrinogen. The aforementioned fibrinogen and fibrinogen-related polypeptides and/or proteins in accordance with certain preferred embodiments of the invention are useful to stop and/or control and/or prevent bleeding, particularly as active ingredients in creams, lotions, pastes, salves, liquids, "glues," especially fibrin glues, and other compositions and/or formulations to stop and/or control and/or prevent bleeding, and in bandages, gauzes, swabs, applicator packs and other articles of manufacture and/or devices for administering, applying, maintaining, covering, working with, protecting, and/or removing creams, lotions, pastes, salves, liquids, glues and other compositions and/or formulations that contain the aforementioned fibrinogen and related polypeptides and/or proteins intended for use to stop and/or control and/or prevent bleeding.

The present invention is further described by reference to the following examples which are provided by way of illustration only and do not themselves depict in their particulars or in any general fashion limitations of the present invention.

EXAMPLES

Example 1

Construction of DNAs for Transgenic Expression of Polypeptides in Saliva

As illustrated below, DNAs, vectors and expression constructs for use in accordance with the invention can be made using standard recombinant DNA techniques, such as those set forth in MOLECULAR CLONING, A LABORATORY MANUAL, Vol. 1-3, Sambrook et al., Cold Spring Harbor Press (1989), which is incorporated herein by reference in its entirety in particular in parts pertinent to making and manipulating genetic material, including polynucleotides, for making and using transgenic animals in accordance with various aspects and embodiments of the invention herein disclosed.

Constructs for transgenic expression of one or more genes, and for production specifically in saliva of one or more polypeptides and/or proteins and/or other substances engendered by expression of the transgene can be made readily using recombinant DNA techniques such as those described in the above-mentioned manual. Typically, the constructs are comprised of three or four functional elements.

(A) DNA containing cis-acting expression signals effective for transcription in salivary gland cells. Preferably, the DNA contains expression control signals effective for efficient transcription in parotid gland cells and/or other major salivary glands that secret relatively large amounts of polypeptides and/or proteins and/or other substances into saliva. Typically, but not always, the expression regulatory regions will be those of a polypeptide and/or protein that is expressed, preferably continuously, at high levels in cells of major salivary glands, preferably parotid glands, and naturally is present at high levels in saliva. The DNA often will be modified to ensure operativity, to facilitate joining the control regions to other elements of the expression construct, and/or to vector DNA, to incorporate or eliminate sites for amplification by PCR and/or other methods, and to facilitate subsequent manipulations in making the construct, and isolating DNA for making transgenic organisms (among other things).

(B) A cDNA or genomic DNA encoding (i) a polypeptide and/or protein to be expressed, in particular, in salivary gland cells, and (ii) a region encoding an operable secretion signal effective to direct secretion of the polypeptide and/or protein into the duct of the gland and into saliva. The secretion signal may be endogenous to the polypeptide and/or protein to be expressed, or it may be heterologous thereto. As disclosed elsewhere herein in greater detail, the polypeptide and/or protein in certain preferred embodiments of the presently disclosed invention is, among others, fibrinogen or thrombin, particularly human fibrinogen or human thrombin. The salivary gland cells in certain preferred embodiments of the invention, as disclosed further elsewhere herein, are cells of a parotid gland.

(C) Termination and 3' regulatory sequences, in particular a polyadenylation signal effective for polyadenylation of the primary transcript in parotid gland cells. An SV40 polyadenylation signal is preferred in some embodiments of the invention, in others a polyadenylation signal of an endogenous gene highly expressed in salivary gland cells is preferred.

The elements A, B and C set out above, may, in practice, occur in two fragments of DNA, or three fragments, or more or less fragments. Whatever number of such fragments, and/or intermediates in the process of making the construct, the elements are joined in operable linkage effective for salivary gland specific expression and saliva-specific expression of the desired polypeptide and/or protein in a DNA construct suitable for transgenesis, generally using standard molecular biology techniques, such as those described in the above-referenced laboratory manual.

Example 2

Preparation of DNAs for Microinjection into Eggs or Embryos

A plasmid vector containing a genetic construct of Example 1 is cloned and propagated in E. coli. Vector DNA is isolated from the E. coli cultures by standard methods of lysis and precipitation, as described for instance in the aforementioned laboratory manual. The expression construct then is prepared for microinjection using state of the art procedures, such as those described in the aforementioned manual and in references discussed in this regard elsewhere herein, as follows. A linear DNA comprising the expression construct is prepared from the plasmid vector by restriction enzyme cleavage or, in some cases, by PCR. The expression construct-containing DNA is separated from other DNA by agarose gel electrophoresis. The separated DNAs are visualized in the gel by fluorescence when electrophoresis is complete. Their sizes of the separated DNAs are determined from their migration distances in the gel using a standard curve based on migration distances of DNAs of known size resolved in the same gel. The expression construct is identified by its size and then excised from the gel, free from other DNA. The expression construct-containing DNA is isolated from the excised agarose by electroelution, and recovered in a small volume of elution buffer. The solution containing the fragment is brought to 10 mM magnesium, 20 mM EDTA and 0.1% SDS and then is extracted with phenol/chloroform. The DNA thereafter is precipitated from the aqueous layer with 2.5 volumes of ethanol in the presence of 0.3 M sodium acetate at −20° C. overnight. After centrifugation, the pellet is washed with 70% ethanol, dried, and resuspended in sterile distilled water. The DNA then is further purified by sucrose gradient centrifugation using standard procedures. DNA concentrations are determined by agarose gel electrophoresis by staining with ethidium bromide and comparing the fluorescent intensity of an aliquot of the DNA with the intensity of standards. Samples are adjusted to 10 µg/ml and stored at −20° C. prior to microinjection. Standard protocols that can be used for gene preparation in this regard are set out in, for example, MOLECULAR CLONING, A LABORATORY MANUAL, Vol. 1-3, Sambrook et al., Cold Spring Harbor Press (1989) which is incorporated herein by reference particularly as to cloning, isolating, purifying and manipulating DNAs for microinjection in accordance with the invention herein described.

Example 3

Transgenic Animal Production (1) Mice

Transgenic mice are produced by pronuclear microinjection using standard techniques as described below.

Glass needles for micro-injection are prepared using a micropipet puller and microforge. Injections are performed using a Nikon microscope having Hoffman Modulation Contrast optics, with micromanipulators and a pico-injector driven by $N_2$ (Narashigi).

Fertilized mouse embryos are surgically removed from the oviducts of super-ovulated female CD-1 mice and placed into M2 medium. Cumulus cells are removed from the embryos by treatment with 300 µg/ml hyaluronidase. The embryos are rinsed after treatment in fresh M2 medium, transferred into M16 medium and stored at 37° C. prior to injection.

Female mice are made pseudo-pregnant by mating with vasectomized males. DNA is injected into the male pronucleus of embryos prepared as described above. The injected embryos are implanted into avertin-anesthetized pseudo-pregnant recipient females. Embryos are allowed to come to term and newborn mice are delivered. The newborn mice are analyzed for the presence and integration of the injected DNA.

(2) Swine

DNAs and injection equipment and supplies are prepared much the same as described for mice. Embryos are recovered from oviducts obtained from healthy female swine. They are placed into a 1.5 ml microfuge tube containing approximately 0.5 ml embryo transfer media (phosphate buffered saline+10% fetal calf serum, Gibco BRL) and centrifuged for 12 minutes at 16,000×g RCF (13,450 RPM) in a microcentrifuge (Allied Instruments, model 235C). The embryos are removed from the microfuge tube with a drawn and polished Pasteur pipette and placed into a 35 mm petri dish for examination. If the cytoplasm is still opaque with lipid such that pronuclei are not visible, the embryos are centrifuged again for 15 minutes. Embryos to be microinjected are placed into a microdrop of media (approximately 100 µl) in the center of the lid of a 100 mm petri dish. Paraffin oil is used to cover the microdrop and fill the lid to prevent media from evaporating. The petri dish lid containing the embryos is set onto an inverted microscope (Carl Zeiss) equipped with both a heated stage and Hoffman Modulation Contrast optics (200× final magnification). A finely drawn (Kopf Vertical Pipette Puller, model 720) and polished (Narishige microforge, model MF-35) micropipette is used to stabilize the embryos while about 1-2 picoliters of purified DNA solution containing approximately 200-500 copies of DNA construct is delivered into the male pronucleus with another finely drawn micropipette. Embryos surviving the microinjection process in good health, as judged by visual examination, are loaded into a polypropylene tube (2 mm ID) for transfer into a recipient pseudo pregnant female swine, which is carried out much as described above.

(3) Cows

Bovine embryos are obtained and injected much as described above for mice and pigs, in accordance with the procedures for cows described in U.S. Pat. No. 6,140,552 which is incorporated herein by reference particularly in parts pertinent to microinjection of DNAs and other methods to produce transgenic bovine animals.

Example 4

Assessing Construct Integration

Integration and/or alteration of host cell genomic content and/or organization to assess transgenesis and transgenic alterations is assessed by standard techniques as follows.

(1) Preparation of DNA from Tissue Samples (2) From Tails and/or Ear Notch Samples A 5 mm piece of mouse tail is removed from each potentially transgenic mouse at weaning (3 weeks of age), minced, and treated with proteinase K and SDS at 37° C. overnight. The mixture then is incubated with DNase-free RNase at 37° C. for 1-2 hours. In some cases the mixture is extracted extensively with phenol/chloroform. DNA is precipitated from the mixture with sodium acetate and ethanol at −20° C. overnight, collected by centrifugation, washed in 70% ethanol and then is dried. The dried DNA pellet is used directly for PCR. A similar procedure is used to prepare DNA from swine and bovine animals, except that DNA is isolated from ear notch tissue instead of tail.

(2) From Saliva

Alternatively, but less favorably in most cases, transgene insertion and integrity in animals is assessed by PCR using DNA prepared from saliva much as described by Irwin et al. (1996), *Nature Biotechnology* 14(9): 1146-1148, which is incorporated herein by reference in its entirety particularly as to methods for using saliva to detect and analyze transgenesis in accordance with the invention. Although saliva based assay of transgenesis has significant disadvantages, it also has some positive features. Importantly, it can be less stressful than alternatives that depend on invasive or surgical alternatives to obtain cells for analysis, and it can be repeated as many times as desired without negative effects on the animal. For the most part, the saliva based assay is carried out much the same as assays based on DNA from tail or ear notch samples, except that the DNA for analysis is prepared from saliva. Briefly, saliva is obtained from each mouse to be assessed for transgenesis by pipetting a small volume of dilution buffer into the oral cavity and then recovering the resulting solution back into the pipet tip. The sample is spotted onto DNA binding paper and, after washing, DNA on the paper is amplified by PCR. The amplified DNA is detected directly on the binding paper by hybridization and/or analyzed by gel electrophoresis, and purified as described above for DNA from tail and ear notch samples.

(2) Oligonucleotide Probes for PCR Assay

Oligonucleotide pairs are used to prime polymerase chain reactions to detect constructs in the transgenic animals. Oligonucleotide pairs that bridge the target are used to detect the exogenously-derived DNA integrated into cells of the transgenic organisms. Primer pairs that detect endogenous gene sequences but not the microinjected DNA are used as positive controls in the PCR assay. In particular, sets of primers are chosen based upon the sequence of the hybrid vector such that the PCR product incorporates both the promoter and structural gene elements of the transgene and thus distinguish it from naturally occurring genes that otherwise might be amplified, e.g., as would be the case for primers that hybridize to the structural gene alone when the sequences of the endogenous and exogenous structural genes are the same.

(3) PCR Reaction Conditions and Product Analysis

PCR reactions are performed using 40 cycles in an automated temperature cycler (M.J. Research). An annealing temperature of 58° C., a denaturation temperature of 94° C., and an extension temperature of 72° C. 100 ng of oligo primers and 5.0 microgram of (genomic) template DNA are used per PCR reaction. Products of the PCR reactions are analyzed by agarose gel electrophoresis. Fragment sizes are estimated by migration relative to molecular weight standards. The sizes are compared with the sizes expected for the injected constructs to verify the presence of an intact expression construct in the transgenic host.

(4) Results of PCR Analysis of Transgenic Animals

PCR analysis is performed as described immediately above reveals intact expression constructs in the DNA of some mice, pigs and cows that developed from the embryos microinjected with the expression construct-containing DNA. When transgenic animals containing an intact expression construct come of age, they are bred together. The offspring from these matings are examined for the presence of the intact transgene by the same PCR assay. Mendelian transmission of integrated transgenes is verified by PCR in several mice, pigs and cows.

Example 5

Saliva Collection—Transient

For in frequent, intermittent sampling, such as may be used to assess output of the transgene product and ensure that it is sufficiently continuous and constant to warrant continuous collection, saliva is collected using absorbent sponges or aspiration as set out herein above.

Example 6

Saliva Collection—Continuous

For continuous collection of saliva the device and procedures stated herein above are used. Additives that are added to the collection vessel, where and when appropriate, such as for long-term collection, include EDTA, heparin, protease inhibitors, salts and other agents that stabilizes the integrity of the protein at room temperature and within the saliva environment.

Example 7

Quantitative Determination of Transgenic Products in Saliva

Immunological methods such as ELISA assays often can be used to measure the amount of a transgenic product in saliva. ELISAs that use monoclonal antibodies or polyclonal antibodies can be used in this regard. Except for differences in recognition reagents, ELISAs in this regard are essentially the same and can be carried out using procedures like those described below.

A normal non-transgenic bovine animal is used for control saliva samples. A series of concentration standards ranging from 1 ng/ml to 1 mg/ml is prepared by spiking a standard preparation of the protein (of known concentration and activity) into aliquots of the control saliva. The controls and transgenic saliva are analyzed simultaneously in the ELISA assay, as described in greater detail below. The concentration of the protein in the transgenic saliva is estimated by comparing ELISA results for the transgenic saliva with those for the standards.

Microtiter plate wells are coated overnight at 4° C. with 3 μg/ml of a monoclonal antibody in 50 μl of 0.1 M sodium bicarbonate buffer, pH 8.3. Afterward the wells are washed once with TET buffer (0.01 M Tris pH 7.5; 0.01 M EDTA; 0.02%; Tween-20, pH 7.45). They then are blocked with 400 μl per well of 1% BSA in PBS for 1 hour at 37° C. Thereafter the wells are washed with TET buffer five times. 100 μl of sample or control saliva is introduced into the wells. The control saliva is from normal animals and is spiked with various amounts of a reference preparation of the transgenic product, to provide a calibration curve for interpolating the ELISA assay results from the transgenic samples. The samples are incubated in the wells to allow transgenic product-antigen therein to bind to the immobilized antibodies. The wells then are washed five times with TET buffer. Horseradish peroxidase (HRP) conjugated to rabbit antibody specific for the transgenic product is diluted 1:1,000 in 0.1% BSA/TET, 100 μl of the diluted HRP conjugate is added to each well and incubated for 2 hours at room temperature while shaking at 100 rpm. After the incubation, the conjugate-containing solution is removed from the wells. The wells are washed 5 times with TET buffer. Then 1000 of a stock solution of orthophenyldiamine (OPD) is added to each well. (The stock solution is made by dissolving one tablet of OPD in 20 ml of 0.1 M citrate-phosphate buffer, pH 5.0.) The OPD solution is incubated in the wells for 10 minutes at room temperature and then the reaction is stopped by adding 1 N sulfuric acid. The extent of the reaction is determined by measuring optical absorption of the acidified OPD solution in each well at 490 nm.

Fiduciary curves are developed for the ELISA assay using a standard reference preparation of the product. The concentration of the product in the transgenic saliva samples is interpolated from the fiduciary curves. Saliva from normal non-transgenic animals and/or animals transgenic for other products are used for negative controls.

Example 8

Size Assay (A) Gel Electrophoresis

Saliva samples are prepared for gel electrophoresis and western blotting by standard techniques. Molecular weights of proteins in saliva samples are determined by denaturing polyacrylamide gels, using standard techniques. SDS-urea loading buffer is used, and the gels are SDS-polyacrylamide gels. The percent acrylamide and the degree of cross linking of the gels is that of well established methods for resolving the polypeptides and/or proteins of interest in the saliva samples. The saliva samples are analyzed in the gels alongside (1) a blank control from a non-transgenic animal and/or a comparable animal transgenic for an unrelated DNA, (2) control saliva containing an appropriate amount of a standard reference preparation of the polypeptide and/or protein of interest, and (3) molecular weight markers. For quantitative determinations, a fiduciary concentration series of the standard is run alongside the saliva samples from the transgenic animals. Several dilutions of saliva samples are run on some gels for greater quantitative accuracy, as well.

For relatively high protein loadings, the gels are stained with Coomassie Blue. For relatively low protein loadings, the gels are stained with silver stain. The proteins thus visualized in the transgenic samples are compared with the blank control sample, the samples containing the reference preparation, and the molecular weight standards. The absence or the presence of the protein in the transgenic saliva and/or its size and/or its concentration in the saliva is estimated therefrom.

(B) Western Blotting

Proteins separated by size in SDS gels as set out above are transferred onto filter membranes for Western blotting. The filter membranes are processed by standard techniques, and incubated with primary antibody that binds to the protein of interest. Thereafter, the bound antibody is detected much the same as for the above-described ELISA. In brief: unbound antibody is washed away, the filter membrane is incubated with secondary antibody-enzyme conjugate, unbound conjugate is removed, and polypeptides of the protein of interest that bind the primary antibody (or antibody mixture) are visualized by chromogenic reaction of the filter-bound enzyme conjugate. The presence (or absence) and/or the molecular weight(s) and/or the integrity and/or the amount of the protein of interest in the transgenic saliva are estimated by comparing the bands of the transgenic saliva samples with those of the controls and standards.

Example 9

Assay of Posttranslational Modification

Proteins are isolated from saliva samples and subjected to carbohydrate compositional analysis for Fucose, Gal NAc, Glc, NAc, Galactose, Mannose and Sialic Acid by HPLC as described by Denman et al. (1991): *Bio/Technology* 9: 839-843.

GLA-specific ELISA is used to determine GLA modification of proteins transgenically expressed in saliva, in much the same manner as the ELISAs described above. Fiduciary cures for these assays can be prepared by spiking non-transgenic, normal saliva spiked with varying concentrations of a reference preparation of known GLA content, and assaying these samples by the same procedure as the test samples. A mutein lacking Gla regions can be used as a negative control in the assay. Gla-less control samples, normal, nontransgenic reference samples and saliva samples are all analyzed by the same methods. Samples are loaded in 25 mM EDTA onto immunoaffinity columns specific for GLA. Unbound material is washed away and the columns then are treated with several washes of 25 mM $CaCl_2$. Extraneous material is removed in the buffer wash, GLA containing protein is eluted in 25 mM $CaCl_2$, and GLA-less material remains bound to the column even in the presence of the 25 mM $CaCl_2$. Material eluting in each wash is collected and assayed by ELISA using a GLA-specific antibody as described above.

Assays for other post-translational modifications, including amidation, phosphorylation, ADP-ribosylation, lipidation and acetylation are carried out using similar well known and accepted procedures.

Example 10

Amidolytic Activity Assay

20 μL of sample or control is mixed with 80 μL of 1 μg/ml snake venom activator 20 mM Tris HCl, 150 mM NaCl, 0.2% NaAzide, pH 7.4 ("activation buffer"). The mixture is incubated at 37° C. for one hour. 100 μL of 0.25 mM thrombin chromogenic substrate is then added and the color is allowed to proceed for 1 to 3 hours. Absorbency at 450 nm is determined and the activity of each sample is determined by interpolation using a reference curve based on human plasma prothrombin diluted in activation buffer. The amidolytic activity assays are carried out in accordance with the procedures disclosed in U.S. Pat. No. 5,476,777 to Holly et al., *Methods for producing thrombin*, particularly at column 28, lines 33 et seq. in particular, which is incorporated herein by reference in its entirety in parts pertinent to the foregoing description of thrombotic amidolytic activity assay.

Example 11

Production in of Prothrombin in Saliva of Transgenic Cows

Prothrombin and Thrombin

Prothrombin (also called Factor II and F2) is a circulating blood protein. At sites of injury it is converted to thrombin by other factors of the coagulation cascade. Thrombin catalyzes the conversion of fibrinogen to fibrin, and the formation and cross-linking of fibrin clots. Prothrombin thus provides a distributed reservoir of pro-coagulant activity that can be converted immediately at injury sites to initiate clot formation, staunch bleeding and stimulate immune and healing responses. (For a review see PROTHROMBIN AND OTHER VITAMIN K PROTEINS Vols I and II, Seegers and Walz, Eds., CRC Press, Boca Raton, Fla. (1986) which is incorporated herein by reference in its entirety, particularly parts pertinent to prothrombin structure, modification, activity, production, purification, physiological activity, functions and effects, and uses including clinical and non-clinical uses.)

Human prothrombin is fairly typical of mammalian prothrombins. It is a single chain protein. It contains a pro peptide, a gla domain, two kringle regions, an A chain and a serine protease domain. It also contains two sites for cleavage by factor Xa. Prothrombin is activated to thrombin by a series of proteolytic cleavages. The circulating single chain zymogen is activated by Factor Xa complex, which cleaves prothrombin at two sites. Cleavage at the first site liberates a fragment containing the gla domain and the two kringle regions. This N-terminal fragment, referred to as Fragment 1.2, contains the moieties responsible for calcium bridge formation and for the interaction of prothrombin with Factor V. The C-terminal fragment, referred to as Prethrombin 2, is the immediate, thrombotically inactive precursor of thrombin. Prethrombin 2 is activated by the second cleavage by Factor Xa complex. The second cleavage splits Prethrombin 2 into two chains linked by disulfide bonds. The disulfide-linked two-chain molecule is active thrombin. (See, for instance, pages 514-516 in TEXTBOOK OF HEMATOL- OGY, 2nd Edition, Shirlyn B. McKenzie, William & Wilkins, Baltimore (1996) which is herein incorporated herein by reference in parts pertinent to thrombin and prothrombin.)

Prothrombin and thrombin exhibit a variety of post-translational modifications. Many of the modifications regulate activities of the proteins and are important to their physiological functions. Important modifications include proteolytic processing, as described above, glycosylation and glutamic acid γ-carboxylation as discussed further below. Human and bovine prothrombin, for instance, are γ-carboxylated at glutamic acid residues 7, 8, 15, 17, 20, 21, 26, 27, 30 and 33 by a series of vitamin K-dependent enzyme reactions. Mouse and rat have the same sites for glutamic acid carboxylation and likely exhibit the same pattern of γ-carboxylation. (See for instance Degen, *Seminars in Thrombosis and Hemostasis* 18(2): 230-242 (1992) which is incorporated herein by reference in its entirety, particularly as to the foregoing in parts pertinent to γ-carboxylation of prothrombins.) Gamma-carboxylation of some of the residues is required for calcium-dependent membrane binding and thus plays an important role in localizing prothrombin at sites of injury. Gamma carboxylation of other glutamic acid residues modulates interaction and complex formation of prothrombin with other vitamin K-dependent coagulation factors. Physiologically, particularly in humans, it appears that complete-carboxylation is required for activation and conversation of prothrombin to thrombin. Notably, the extent of γ-carboxylation of prothrombin varies markedly from one preparation to another, even for preparations made in the same system according to the same protocol. Although physiological activation of prothrombin requires complete γ-carboxylation, it is not necessary for thrombin activity. In fact, all the sites for prothrombin γ-carboxylation occur in a relatively small region, called the "gla domain," near the carboxyl terminus. Proteolytic cleavage during activation separates the entire gla domain from the regions of prothrombin that form thrombin and, as a result, there are no carboxylation sites in thrombin. Since active thrombin does not require γ-carboxylation it can be derived by chemical and other cleavage methods from prothrombin with or without γ-carboxylation.

Prothrombin also is glycosylated. Human prothrombin contains three sites for N-linked glycosylation: Asn-79, Asn-101 and Asn-378. An additional site, Asn-Leu-Ser at Asn-165, matches the consensus Asn-X-Ser/Thr sequence of N-linked glycosylation; but, does not appear to be glycosylated in human prothrombin. Bovine prothrombin is similarly glycosylated at three sites. Two of the bovine sites, Asn-101 and Asn-378, are the same as human prothrombin; but, the third site in bovine prothrombin is Asn-77 rather than Asn-79. Mouse prothrombin has five sites for N-linked glycosylation: Asn-79, Asn-101, Asn-165, Asn-378 and Asn-518. Rat prothrombin also has five sites. Four are identical to mouse; but, one is different: Asn 79 rather than 77. The mouse and rat sites at Asn-165, analogous to the human site, probably are not glycosylated. The extent and types of glycosylation observed at these sites varies considerably in all organisms in which it has been studied. (For instance see Degen, *Seminars in Thrombosis and Hemostasis* 18(2): 230-242 (1992) which is incorporated herein by reference in its entirety, as to the foregoing particularly with regard to glycosylation of prothrombins.) Glycosylation plays an important role in activity and physiological function and effects of prothrombin. Generally, glycosylation can affect enzymatic activity, substrate preferences, binding to cofactors and other moieties, complex formation, thermal stability, resistance to proteases and physiological persistence among other things. (For instance see PROTHROMBIN AND OTHER VITAMIN K PROTEINS Vols I and II, Seegers and Walz, Eds., CRC Press, Boca Raton, Fla. (1986) which is incorporated herein by reference in its entirety, as to the foregoing particularly in parts pertinent to glycosylation of prothrombin, especially in this regard Vol. 1, Chapter 8, Kobata and Mizuochi, *Current Status of Carbohydrate Constituents and Prospects,* 81-94.)

Currently, there is no entirely satisfactory way to produce prothrombin and/or thrombin that is commercially advantageous and/or economically viable. The following example illustrates the invention in this regard as to the production of prothrombin and/or thrombin in the saliva of transgenic ruminant mammals, cows in particular.

(1) DNA Constructs

DNAs, vectors and expression constructs for use in expressing prothrombin and/or thrombin in saliva of transgenic cows in accordance with the invention can be made as described above using standard recombinant DNA techniques, such as those set forth in MOLECULAR CLONING, A LABORATORY MANUAL, Vol. 1-3, Sambrook et al., Cold Spring Harbor Press (1989), which is incorporated herein by reference in its entirety. Using such methods, the cis-acting expression signals of genes for proteins that occur in high abundance in salivary gland cells and/or saliva are operatively fused to DNAs encoding human prothrombin for introduction into and expression in transgenic cows.

A full-length human prothrombin sequence in the GenBank database (Accession Number J00307) is used to design probes that can be used to obtain DNAs encoding human prothrombin by conventional means by screening a human liver cDNA library or a human genomic DNA library and purifying therefrom a full-length prothrombin cDNA using methods much the same as those described by MacGillivray et al., *Ann. N.Y. Acad. Sci.* 485: 73-79 (1986); Jorgensen et al., *Circulation* 74(Supp2): 1637 (Abstract) (1986); Degen et al., *DNA Cell Biol.* 9: 487-498 (1990); Degen et al., *Biochemistry* 22: 2087-2097 (1983); and U.S. Pat. No. 4,476,777 of Holly et al. on *Methods for Producing Thrombin,* each of which is incorporated herein by reference in its entirety, particularly as to the foregoing in parts pertinent to obtaining DNAs encoding prothrombin and related polypeptides, especially genomic and cDNAs encoding the full length of human prothrombin. Human prothrombin-specific probe sequences are designed using the GenBank full length human prothrombin sequence and standard software. The probe sequences are used to search the dbEST database to identify the most full length human prothrombin-encoding cDNA clone in the IMAGE consortium library. The longest clone is identified and, if it is not complete, a full length cDNA clone is isolated by routine techniques of gene cloning, using as probes primers based on sequence information from the databases and/or IMAGE or other cDNA clones or fragments thereof.

The sequence of the cDNA is verified by re-sequencing. The cDNA then is cloned into an expression cassette and an expression vector for propagation and to prepare DNA for injection.

(2) DNA Purification for Microinjection

A human prothrombin cDNA expression cassette for expression in cows is prepared as follows. Linear DNA for injection is severed intact from other parts of the vector by restriction enzyme cleavage, and the fragments are resolved from one another by agarose gel electrophoresis. The expression cassette-containing fragment is cut from the gel and isolated from the gel plug by electroelution. The solution containing the DNA is brought to 10 mM magnesium, 20 mM EDTA and 0.1% SDS and extracted with phenol/chloroform. The DNA then is precipitated from the aqueous layer with 2.5 volumes of ethanol in the presence of 0.3 M sodium acetate at −20° C. overnight. After centrifugation, the pellet is washed with 70% ethanol, dried, and resuspended in sterile distilled water. The DNA then is further purified by sucrose gradient centrifugation or by other methods using standard procedures. DNA concentrations of purified DNAs are determined by agarose gel electrophoresis by staining with ethidium bromide and comparing the fluorescent intensity of an aliquot of the DNA with the intensity of standards. Samples are adjusted to 10 µg/ml and stored at −20° C. prior to microinjection.

(3) Embryo Injection

Cow embryos are obtained and injected as described above. Injected embryos are implanted as described above.

(4) Detection of Transgenic DNA

The presence of DNA in cows from injected embryos is detected by PCR, much as described above.

(5) Saliva

Saliva samples are obtained from transgenic cows using the methods described elsewhere herein.

(6) Elisa

To assay the presence and amount of prothrombin in saliva from the transgenic cows, saliva samples are diluted 1:2 in prothrombin dilution buffer (40 mM Tris/200 mM EDTA/200 mM NaCl, pH 7.4), centrifuged at 14,000 rpm in a microcentrifuge for 30 minutes at 4° C., and then chilled at 4° C. until use. ELISA assays are used to measure the amount of prothrombin in samples from transgenic animals. One ELISA uses a monoclonal antibody, 7D7B10, that specifically recognizes the amino terminal region of prothrombin. The other ELISA uses a polyclonal anti-human Prothrombin antiserum. Except for the difference in the recognition reagent, the ELISAs are essentially the same and are carried out using the procedure detailed below.

Microtiter plate wells are coated overnight at 4° C. with 3 µg/ml of the monoclonal antibody in 50 µl of 0.1 M sodium bicarbonate buffer, pH 8.3. Afterward the wells are washed once with TET buffer (0.01 M Tris pH 7.5; 0.01 M EDTA; 0.02%; Tween-20, pH 7.45). They then are blocked with 400 µl per well of 1% BSA in PBS for 1 hour at 37° C. Thereafter the wells are washed with TET buffer five times. 100 µl of sample or control saliva is introduced into the wells. The control saliva is from normal animals and is spiked with various amounts of a reference prothrombin preparation to provide a calibration curve for the ELISA results. The saliva samples are incubated in the wells to allow prothrombin therein to bind to the immobilized prothrombin-specific antibodies. The wells then are washed five times with TET buffer. Horseradish peroxidase (HRP) conjugated to rabbit anti-prothrombin is diluted 1:1,000 in 0.1% BSA/TET, 100 µl of the diluted HRP conjugate is added to each well and incubated for 2 hours at room temperature while shaking at 100 rpm. After the incubation, the conjugate-containing solution is removed from the wells. The wells are washed 5 times with TET buffer. Then 100 µl of a stock solution of orthophenyldiamine (OPD) is added to each well. (The stock solution is made by dissolving one tablet of OPD in 20 ml of 0.1 M citrate-phosphate buffer (pH 5.0).) The OPD solution is incubated in the wells for 10 minutes at room temperature and then the reaction is stopped by adding 1 N sulfuric acid. The extent of the reaction is determined by measuring optical absorption of the acidified OPD solution in each well at 490 nm.

Fiduciary curves are developed for the ELISA assay for both the monoclonal and the polyclonal reagents using a standard preparation of human prothrombin. The concentration of prothrombin in the saliva samples from which they are derived is interpolated from the fiduciary curves. Saliva from normal non-transgenic cows or cows transgenic for other proteins obtained and, treated the same as saliva from the test animals is used for negative controls.

Results obtained by the two ELISAs are in close agreement. Almost all of the animals that are shown by PCR to be transgenic for the human prothrombin provide significant levels of prothrombin in their saliva, generally between 0.5 to 5.0 mg/ml.

(7) SDS-page

Prothrombin in saliva samples from transgenic cows is analyzed by SDS-PAGE and western blotting, as described elsewhere herein. 5 µl of each sample is diluted to 100 in SDS-PAGE Tris/glycine reducing cocktail, providing 1 µl of saliva per 20 µls loaded onto the gel. A human prothrombin standard (Enzyme Research Laboratories, South Bend, Ind.) is run alongside the saliva samples, diluted to 5 ng/µl in reducing cocktail (100 ng/lane). A thrombin standard also is run in the same way. Saliva from non-transgenic animals, prepared and diluted identically to the transgenic samples, is run for negative controls. Additionally, saliva from cows transgenic for other proteins also is run as negative control. For quantitative estimates of expression levels, multiple dilutions of both the transgenic saliva sample and human reference material of known concentration are run alongside one another. Samples are resolved on pre-cast 7.5% polyacrylamide gels (Bio-Rad, Hercules, Calif.) and electrophoresed at 200V until the dye front is at or just eluting off the bottom of the gel. Gels are stained to visualize proteins using Coomassie Blue and/or blotted onto membranes for immunospecific detection of prothrombin as follows.

(8) Westerns

The separated proteins are transferred from the gels onto PVDF membranes (Bio-Rad) using the Novex X-Cell II™ Blot module (Invitrogen, Carlsbad, Calif.) according to manufacturer's recommendations. Transfers are for 18 to 24 hr. After transfer, membranes are blocked in TBST-Casein (25 mM Tris, pH 7.2/50 mM NaCl/0.05% Tween 20/0.5% Casein) for 1-3 hours at 37° C. Sheep anti-human prothrombin antibody (ERL) is added to the blocking buffer at a 1:1000 dilution and membranes are allowed to incubate for at least one additional hour. The primary antibody solution is decanted, the membranes are extensively washed in deionized water, and they then are placed in a fresh aliquot of blocking buffer. Thereafter, donkey anti-sheep antibody conjugated to horseradish peroxidase (Sigma, St. Louis, Mo., product number 3415) is added at 1:1000 dilution, and the membranes are incubated for 30-75 minutes at 37° C. Following the incubation the membranes are extensively water washed. Then color is developed using a metal-enhanced DAB kit (Pierce, Rockford, Ill.). At the end of the color reaction, before further handling, the blots are thoroughly dried on filter paper. To quantify the results, membranes are scanned using a Shimadzu CS-9000 dual-wavelength, flying spot densitometer (350 nm, 0.4×5 mm beam size).

(9) Amidolytic Activity

20 µl of sample or control is mixed with 80 µl of 1 µg/ml snake venom activator 20 mM Tris HCl, 150 mM NaCl, 0.2% NaAzide, pH 7.4 ("activation buffer"). The mixture is incubated at 37° C. for one hour. 100 µl of 0.25 mM thrombin chromogenic substrate is then added and the color is allowed to proceed for 1 to 3 hours. Absorbance at 450 nm is determined and the activity of each sample is determined by interpolation using a reference curve based on human plasma prothrombin diluted in activation buffer. Regarding amidolytic activity assays of this type see, for instance, U.S. Pat. No. 5,476,777 to Holly et al. for Methods for producing thrombin, column 28, lines 33 et seq. in particular, which is incorporated herein by reference in its entirety in parts pertinent to the foregoing description of thrombotic amidolytic activity assay.

(10) GLA Content

Standard ELISAs are performed to assay prothrombin in saliva from transgenic animals. Normal human prothrombin is spiked into normal saliva at varying concentrations and assayed by the same protocol. Finally, prothrombin without Gla regions is assayed by the ELISA assay. All three types of samples are loaded in 25 mM EDTA onto immunoaffinity columns specific for GLA. Unbound material is washed away and the columns then are treated with several washes of 25 mM $CaCl_2$. Material eluting in each wash is collected and assayed by the prothrombin ELISA. GLA-less prothrombin remains bound to the column in the presence of $CaCl_2$. Standard GLA eluates in the presence of $CaCl_2$. Prothrombin in saliva from transgenic animals behaves like the normal prothrombin. The results indicate that the transgenic prothrombin is γ-carboxylated like the native molecule.

(11) Yield 48 saliva samples from 12 different transgenic cows are analyzed for the presence of transgenic prothrombin and/or thrombin (4 samples taken at different times from each cow). Prothrombin is detected in all of the samples from 7 cows, in the last 3 of 4 samples from one cow, and in only the first 2 of 4 samples from another cow. Overall, 9 or the 12 cows produce prothrombin in their saliva, at some time points. Of these, 8 appear to produce prothrombin continuously in their saliva. Prothrombin from all 8 producer cows exhibits prothrombin amidolytic activity and gla content substantially the same as human prothrombin.

(12) Breeding

Cows that are determined to be transgenic by PCR are bred and allowed to complete gestation.

Example 11

Production in of Fibrinogen in Saliva of Transgenic Cows

Fibrinogen

The invention herein described is further illustrated by the following specific embodiment in which human fibrinogen is produced in saliva of transgenic cows.

Fibrinogen is a soluble protein of high molecular weight that occurs normally in circulating blood and in plasma. It is the major structural protein in blood clots and plays a central and essential role in the processes of hemostasis and thrombosis Accordingly, it is of considerable medical interest and as a medicament. Fibrinogen, even in its simplest form is a fairly complex protein. Physiologically, it is even more complex. It undergoes a variety of proteolytic processes in normal physiological processes that give rise to a family of processed fibrinogen proteins, polypeptides and "fibrinopeptides." Transgenic expression may be aimed at some but not all of these products; but, must be designed with them in mind.

Human fibrinogen is made up of six polypeptides: two each of three different chains called the A-alpha, B-beta, and gamma chains. The six polypeptides are arranged in fibrinogen as a pair of identical trimers. Each trimer contains one A-alpha, one B-beta and one gamma polypeptide. The A-alpha, B-beta and gamma polypeptides in each polypeptide are held together by several disulfide bonds. The two trimers are bonded together by three additional disulfide bonds, one formed between the two A-alpha chains and two formed between the two gamma chains. The protein is soluble in this form and circulates freely in the blood.

Fibrinogen serves as the precursor to fibrin and thus to clot formation. It is converted to fibrin by thrombin at sites of injury. Thrombin cleaves fibrinogen near the ends of each A-alpha and each B-beta chain, releasing fibrinopeptide As from the amino terminal end of each A-alpha polypeptide and fibrinopeptide B from the amino terminal end of each B-beta polypeptide. The resulting protein, referred to as the fibrin monomer, not only is considerably less soluble than fibrinogen, but also self-assembles (polymerizes, in a manner of speaking) into the insoluble "fibrin matrix" that serves as the principle component of clots. Fibrin is cross linked in the matrix by the Faxtor XIIIa. Ultimately, all going well, the clot is removed by the fibrinolytic system, a process mediated primarily by the proteolytic activity of plasmin on fibrin in the cross-linked fibrin matrix.

While a variety of modified forms of fibrinogen have been developed, and work has been carried out to develop fibrinogen derivatives, fibrinogen produced transgenicly in saliva— in whatever form or variety—to be useful for many clinical purposes should have the aforementioned activities important to its use, including, for instance, its biophysical properties that affect its circulation in the blood, its interaction with thrombin, and its substrate interaction with plasmin and other components of the fibrinolytic system.

Toward this end, transgenic cows are made that produce fibrinogen in their saliva, and the fibrinogen is characterized for comparison with natural human fibrinogen as set out below. The materials and techniques in the work described in this example are readily available and well known to those skilled in the pertinent arts. Many of the methods are described in U.S. Pat. No. 6,037,457 to Susan T. Lord, *Method for recombinant fibrinogen production*, issued on Mar. 14, 2000 (referred to herein as the '457 patent), which relates to expression of fibrinogen polypeptides and proteins in cultured cells and in milk of transgenic animals, which is incorporated herein by reference in its entirety particularly in parts pertinent to methods of making fibrinogen expression constructs, techniques and processes for isolating and purifying fibrinogen polypeptides and/or proteins, and assays and procedures for detecting and measuring characteristics and activities of fibrinogen polypeptides and/or proteins.

Except as noted otherwise in the following example, chemicals and other materials are obtained from commercial suppliers and are reagent grade or superior quality and purity.

(1) Expression Construct

The expression vector is constructed as described in the foregoing examples, particularly Example 1. Briefly, cloned genes for the normal A-alpha, B-beta and gamma polypeptides of human fibrinogen are obtained much as described in Binnie et al. (1993), *Biochemistry* 32: 107 et seq. and in the '457 patent. The identify of the DNAs is verified by DNA sequencing. DNA containing the genes is prepared from clones and then ligated to DNA containing regulatory sequences for expression in bovine parotid glands, much as described elsewhere herein. Three expression cassettes are made, one for salivary gland specific expression of each fibrinogen polypeptide. Constructs are made for propagating just one of the cassettes, or all three cassettes together. DNA for injection to make transgenic cows is prepared from the cassette linearized by restriction and purified by agarose gel electrophoresis and electro-elution, and then by other steps as appropriate, as described above. DNA from the constructs containing individual cassettes, or from the construct containing all three cassettes together is injected as described below.

(2) DNA for Injection

The vector(s) is digested with restriction enzymes to release the DNA for injection from other parts of the construct. The reaction mixture is subjected to electrophoresis on an agarose gel to separate the DNA fragment for injection from other fragments. The band corresponding to the DNA for injection is cut out and subjected to Agarase treatment. Following Agarase treatment the reaction mixture is layered onto a NaCl step gradient (5% to 25% in 2.5% intervals) and centrifuged at 25,000 rpm for 6 hrs at 25° C., as described by Chin-Tih, *Biotechniques* 10(4): 446-450 (April 1991). 0.5 ml fractions are collected from each tube following centrifugation. 10 µl of each fraction is subjected to agarose gel electrophoresis to identify the fractions that contained the DNA for injection. Fractions containing the DNA to be injected are pooled and dialyzed for 45 minutes against ultrapure water. The DNA then is precipitated from the dialyzed sample with $NaClO_4$ and isopropanol, and collected by centrifugation. The pellet containing the DNA is resuspended in injection buffer to a final concentration of 3-5 µg/ml for microinjection.

(3) Embryo Injection

Cow embryos are obtained and injected, and the injected embryos are implanted as described in Examples above.

(4) Detection of Transgenic DNA

The presence of the injected DNA in cows from injected embryos is detected by PCR using primers specific to the injected DNA using methods described in Examples above. In brief, tissue is obtained from the cows and assayed for the presence of the injected DNA by PCR as described above. PCR is carried out using primers specific to the injected DNA and designed so that only DNA from animals incorporating copies of the injected DNA as a transgene yields a PCR product. The PCR reaction products are resolved by agarose gel electrophoresis and visualized by ethidium bromide staining and fluorescence under IN light.

(5) Breeding of Transgenic Cows

Animals that are determined to be transgenic by PCR are bred and offspring are assessed for the presence of the transgenic, its size and its copy number, as set out above.

(6) Saliva Collection

Saliva is collected from cows at regular intervals. Saliva collection is by sponge or aspiration for small to intermediate volumes. Larger volumes are collected via cannula from the duct lumen of one of the cow's parotid glands. Standard surgical procedures and equipment are used to implant the cannula. PMSF and other protease inhibitors are added to the saliva immediately upon collection, and the pH, ionic strength and other parameters of the solution are adjusted for storage, or for immediate use, as needed. Saliva is kept at −80° C. for long term storage.

In some cases, the saliva is clarified before analysis. Typically this is done by diluting the saliva 1:2 in a suitable buffer (for example, 40 mM Tris/200 mM EDTA/200 mM NaCl, pH 7.4), and the diluted samples are centrifuged at 14,000 rpm in a microcentrifuge for 30 minutes at 4° C. The clarified saliva is removed from pelleted material and placed in a clean tube for storage or analysis.

(7) ELISA

Saliva is assayed by ELISA to determine the presence in saliva, and, if it is present, the concentration, of transgenically produced fibrinogen. The assays are carried out, much as described above for other proteins, generally in accordance with the ELISAs in the '457 patent, using a primary antibody specific for fibrinogen. Saliva containing relatively high concentrations of fibrinogen is subjected to further ELISA to determine concentrations. Fibrinogen from the highest producing cows is analyzed further as set out below.

(8) Gel and Western Blot Analysis

The molecular weights and distribution of fibrinogen polypeptides and proteins from transgenic saliva is compared with human plasma-derived fibrinogen by SDS polyacrylamide gel electrophoresis and western blotting. Samples are resolved under reducing conditions on 6% gels, and under non-reducing conditions on 10% gels. Gels are loaded, run and Coomassie Blue stained using standard methods, such as those in Sambrook et al. referenced above. Western Blots are carried out much as described in Binnie et al. (1983), *Biochemistry* 32: 107 et seq. Polyclonal anti-fibrinogen is obtained from a commercial supplier. Monoclonal antibodies specific to the A-alpha, B-beta and gamma changes are in accordance with, respectively, Koppert et al. (1985), *Blood* 66: 503 et seq., Valenzuela et al. (1992), *Amer. J. Pathol.* 141: 86 et seq, and Shiba et al. (1991) *Amer. J. Physiol.* 260. Goat-anti rabbit and goat-anti alkaline phosphatase conjugates are obtained from commercial suppliers. Blots are carried out on 0.45 µm nitrocellulose.

Under non-reducing conditions both samples resolve into two bands of the same MW weight: the slower corresponding in MW to intact fibrinogen, the faster corresponding to "Low Molecular Weight Fibrinogen," a slightly truncated form of fibrinogen lacking a short C-terminal fragment of the A-alpha chains, described in Hohn et al. (1985) *Thromb. Res.* 37: 165 et seq. All of the bands are detected by all of the antibodies.

Under reducing conditions, the saliva and plasma-derived fibrinogens give rise to substantially the same results. The preponderant majority of the material in each sample resolve into three bands with molecular weights corresponding to the A-alpha, B-beta and gamma polypeptides. A few minor bands also appear in both samples. Results are substantially the same for the saliva-derived transgenic fibrinogen and the plasma-derived human fibrinogen standard. The heterogeneous anti-fibrinogen antibody detects all the bands. The A-alpha polypeptide-specific antibody detects only the band corresponding in MW to the A-alpha polypeptide. The B-beta polypeptide-specific antibody detects only the band corresponding in MW to the B-beta polypeptide. The gamma polypeptide specific antibody detects only the band corresponding in MW to the gamma polypeptide.

(9) Yield of Transgenic Cows

About 2,500 oocytes are obtained from healthy female cows. About 2,300 are found to be apparently healthy mature oocytes and are fertilized. From these about 1,400 fertilized 1-cell embryos are obtained. Of these, about 1,200 appear to be healthy and are injected. Approximately 1,000 of the injected embryos initially survive and 687 progress to cleavage. Of these 687 cleavage stage embryos, 140 that appear most likely to be undamaged, normal and healthy are transferred into females for gestation. Pregnancies result in 21 of the implanted female, and these females give birth to 18 calves. Of these 18 offspring, 5 are shown to be transgenic for the injected DNA by transgene-specific PCR, as described in the foregoing Examples. Copy numbers of the injected DNA in the offspring is estimated by Southern analysis as described above.

(10) Purification by Precipitation and Protamine-Sepharose Column (a) Ammonium Sulfate Precipitation Fibrinogen is purified by the method of Binnie et al. (1993), Biochemistry 32: 107 et seq. much as modified in the '457 patent.

Frozen saliva, if used, is placed in a 37° C. water bath until just before it is completely thawed and then it is immediately placed on ice and is maintained at 4° C. until use. All steps in the purification are carried out at 4° C. In addition, all buffers contained a mixture of protease inhibitors Fibrinogen is precipitated from saliva by ammonium sulfate precipitation as follows. Saliva is adjusted to 50 mM Tris-HCl pH 7.6, 100 mM NaCl, 200 mM. ε-ACA, 80 mM EDTA, 400 U aprotinin/ml, 40 muM pepstatin, 40 muM leupeptin, 200 mM benzamidine. Saturated ammonium sulfate is slowly stirred into the buffered saliva to a final concentration of about 40% saturation, and then stirred overnight. The precipitate is collected by centrifugation (16,000×g, 30 min), and then washed several times in fresh ammonium sulfate. After the final wash the precipitate is collected, drained of supernatant, and dissolved in 50 mM Tris-HCl pH 7.3, 150 mM NaCl, 5 mM ε-ACA, 2 mM EDTA, 10 U/ml aprotinin, 1 uM pepstatin, 1 uM leupeptin, 100 uM PMSF, 5 mM benzamidine. The solution, is clarified of residual insoluble material by centrifugation, and the superjacent, containing the partially purified fibrinogen, is transferred to a fresh container for storage until further use.

(b) Protamine-Sepharose Chromatography

Fibrinogen is further purified by protamine-SEPHAROSE® chromatography in accordance with Dempfle et al. (1987), *Thromb. Res.* 46: 19 et seq. After loading and washing the column as described in Dempfle et al, fibrinogen is eluted from the column, and the fibrinogen-containing eluate is neutralized, dialyzed, and stored at −80° C. in buffer containing strong protease inhibitors.

(11) Purification by Precipitation and Immunoaffinity Column (a) Ammonium. Sulfate Precipitation Fibrinogen is precipitated from saliva of transgenic cows as set forth, with the following modifications. Saliva initially is adjusted to 20 mM MES pH 5.6, 100 mM NaCl, 200 mM. ε-ACA, 80 mM EDTA, 10 μl/ml soybean trypsin inhibitor, 40 muM pepstatin, 40 muM leupeptin, 200 mM benzamidine, and 10 ul/ml soybean trypsin inhibitor is used in all the other buffers instead of aprotinin.

(b) Immunoaffinity Chromatography

Following resuspension as described in the foregoing example, ammonium sulfate precipitates are further purified by immunoaffinity chromatography on a column of SEPHAROSE 4B®—coupled to a monoclonal antibody specific for human fibrinogen, much as described by Takebe et al. (1995), *Thromb Haemost* 73: 662 et seq. The antibody preparation for the column is prepared by standard monoclonal antibody methods, and is coupled to CNBr-activated SEPHAROSE 4B™ in accordance with the suppliers instructions. The column is washed thoroughly and equilibrated in 20 in M Tris-HCl pH 7.4, 0.3M NaCl, 1 mM $CaCl_2$. Prior to loading, fibrinogen samples are diluted to approximately 0.5 mg/ml in 20 mM Tris-HCl pH 7.4, 0.3M NaCl, 1 mM $CaCl_2$, 5 mM ε-ACA, 1 uM pepstatin, 1 uM leupeptin, 100 uM PMSF, 5 mM benzamidine, and 10 U/ml soybean trypsin inhibitor. Columns are washed with 20 mM Tris-HCl pH 7.4, 0.3M NaCl, 1 mM $CaCl_2$ and then with 50 mM sodium acetate, pH 6.0, 0.3M NaCl, 1 mM CaCl. Fractions containing the fibrinogen eluate are clarified by centrifugation and then dialyzed against 20 mM HEPES pH 7.4, 0.15M NaCl, 1 mM $CaCl_2$ at 4° C. The dialysate is clarified by centrifugation and the clarified solution containing immunoaffinity-purified fibrinogen is aliquoted and stored at −70° C.

(12) Purified Fibrinogen—Gel and Western Analysis

The molecular weights and distribution of fibrinogen polypeptides and proteins from transgenic saliva are compared with human plasma-derived fibrinogen by SDS polyacrylamide gel electrophoresis and western blotting. Under non-reducing conditions both samples resolve into two bands of the same MW weight: the slower corresponding in MW to intact fibrinogen, the faster corresponding to "Low Molecular Weight Fibrinogen," a slightly truncated form of fibrinogen lacking a short C-terminal fragment of the A-alpha chains, as described in Holm et al. (1985) *Thromb. Res.* 37: 165 et seq. Under reducing conditions, the saliva and plasma-derived fibrinogens give rise to substantially the same results. The preponderant majority of the material in each sample resolve into three bands with molecular weights corresponding to the A-alpha, B-beta and gamma polypeptides. A few minor bands also appear in both samples. Western blots of both reducing and non-reducing gels are probed with fibrinogen, A-alpha, B-alpha and gamma-specific antibodies, using the methods described above. Results are substantially the same for the saliva-derived transgenic fibrinogen and the plasma-derived human fibrinogen standard. The A-alpha, B-beta and gamma-specific antibodies each reacts with a single predominant band in reducing gels, corresponding in molecular weight to the expected antigen. All three bands are visualized by a heterogeneous anti-fibrinogen IgG antibody mixture. A number of minor bands also are seen with all of the antibodies. All of the antibodies visualizes the same two bands in non-reducing bands seen in the stained gels.

(13) Thrombin-Activated Polymerization

The ability of fibrinogen to polymerize, and thus to form clots, is measured by change in turbidity of a fibrinogen-containing sample over a time course initiated by adding thrombin. The polymerization of samples containing fibrinogen made in saliva of transgenic cows is compared with the polymerization of human plasma-derived fibrinogen. Reactions are carried out in the same way as the fibrin release assays described above, except that the buffer contains 0.1 mM $CaCl_2$ instead of 2 mM. Reactions are carried out at 25° C. Turbidity is measured at 350 nm in a thermostated cuvette and recorded using a UV-Viz spectrophotomer equipped with a data capture module and chart recorder. Prior to assay, samples are adjusted to 20 mM HEPES pH 7.4, 0.15M NaCl, 5 mM s-ACA, 0.1 mM $CaCl_2$ by dialysis, and fibrinogen concentrations are adjusted to 0.1 mg/ml. 10 ul of Thrombin (1 U/ml) is added to 90 ul of the fibrinogen sample in a cuvette. Turbidity is measured continuously from just before addition of thrombin until the end of the incubation. The results obtained with fibrinogen produced in transgenic saliva are substantially the same as those obtained with human plasma-derived fibrinogen.

(14) Thrombin Activation: Fibrinopeptide Release

The ability of the transgenic fibrinogen to serve as a substrate for, thrombin activation is assessed by fibrinopeptide release assays. Thrombin-fibrinopeptide release assays are carried out in accordance with Ng et al. (1993), *Methods Enzymol.* 222: 341 et seq., and Haverkate et al. (1986), *Thromb. Haemostasis* 55: 131 et seq. each of which is incorporated herein by reference in its entirety particularly in parts pertinent to peptide release assays in this regard. Samples are incubated with thrombin, and fibrinopeptides released by thrombin activation, FpA and FpB in particular, are resolved by reverse phase HPLC and quantified, as follows. Protease inhibitors are removed from the samples prior to analysis by dialysis against 50 mM Tris-HCl pH 7.4, 150 mM NaCl three times at 4° C. for 20 hours using dialysis tubing with a molecular weight cut off of 12,000-14,000 daltons. Concentrations of the purified fibrinogen samples are determined by absorbance at 280 nm and 320 nm as described by Mihalyi (1968), *Biochemistry* 7: 208 et seq. Samples are diluted in 2 ml at room temperature. At zero time, human thrombin is added to a final concentration of 0.043 U/ml, the reactions are gently vortexed, and rapidly aliquoted into individual tubes for time points. Reactions were stopped in a water bath at just under boiling temperature for at least 8 minutes. Prior to HPLC samples were cleared by centrifugation. Storage was at −20° C. Peptides in each aliquot are separated and quantified by reverse phase HPLC. FpA and FpB are similarly the preponderant peptide product detected in the aliquots from both transgenic salivary fibrinogen and the human plasma protein. The kinetics of FpA and FbB release in the samples is substantially the same in the samples from transgenic saliva and human plasma, and is within the range expected for normal human plasma-derived fibrinogen.

(15) Fibrin Polymerization (a) Monomers

Fibrin monomers are prepared from transgenic saliva-derived fibrinogen essentially as described by Belitser et al. (1968), *Biochim. et Biophys Acta* 154: 367 et seq. Purified fibrinogen is dialyzed against 20 mM HEPES pH 7.4, 0.15M NaCl, 5 mM ε-ACA overnight at 4° C., and then diluted to 0.3 mg/ml in the same buffer. The solution is placed on ice. Thrombin is diluted in the same buffer to 1.1 U/ml and immediately thereafter added to the fibrinogen solution in 1:10 v/v ratio to initiate proteolysis and fibrin generation. The mixture is gently and briefly vortexed and then incubated 3 hours at 37° C. Polymerized fibrin is spooled from the reaction on a glass rod and then washed 10 times in 0.15M NaCl, 5 minutes for each wash, to remove proteolysis buffer completely. Monomers are recovered by dissolving the washed fibrin in ice-cold, 0.125% acetic acid. The monomers are re-polymerized by diluting them 10-fold in 20 mM HEPES pH 7.4, 0.15M NaCl, 5 mM ε-ACA and then incubating them for 3 hours at room temperature for 3 hours as above. The clotting and monomerization procedures are repeated twice more. The final monomer solution is clarified by centrifugation and then allowed to stand for several days at 4° C. to allow residual fibrin polymers to dissociate. Fibrin monomers are stored at 4° C. for up to a month.

(b) Polymerization

The polymerization of fibrin monomers from fibrinogen produced in transgenic saliva is compared to the polymerization of monomers from human serum fibrinogen. Polymerization is measured by turbidity, taken as absorption at 350 nm. Equipment and conditions are the same as those for the thrombin activation turbidity measurements described above, except that the buffer contains 0.1 mM $CaCl_2$. Polymerization is initiated by diluting the monomers into reaction buffer. The relative volumes and concentrations are set up so that monomer concentration in the reaction is sufficient and the buffer maintains neutral pH throughout the reaction after addition of the 0.125% acetic acid solution containing the monomers. Results for the different samples are compared to one another for two quantitative parameters: (1) the lag time before measurable turbidity is produced, which is a measure of the rate of proto-fibril formation, and (2) the maximum slope, which indicates the maximum rate of the reactions. Data for the monomers from the transgenic fibrinogen are substantially similar to the data from human-serum derived fibrinogen in both respects; although the lag period for the transgenic monomers was slightly longer and the maximum slope was about 1.3 times as steep, on average.

(16) CROSS-Linking by $XIII_A$

The ability of Factor Ma to cross link fibrin clots formed by fibrinogen produced in transgenic cow saliva is compared to that of human plasma fibrinogen, to determine the bio-activity of the transgenic clots in this regard, relative to the bio-activity of clots formed by human plasma fibrinogen. The kinetics of cross-linking are measured for each sample. Cross-linking clotting reactions are carried out by polymerizing fibrinogen samples at 0.4 mg/ml with Factor Mita at 1.0 U/ml. Control reactions are carried out the same way, but without Faxtor XIIIa. Reactions are initiated by adding human thrombin to a final concentration of 1 U/ml. All reactions are carried out at room temperature, in 20 mM HEPES pH 7.4, 150 mM NaCl, 5 mM. ε-ACA, 1 mM $CaCl_2$. SDS and β-mercaptoethanol were added to a final concentration of 1% and 2%, respectively, to stop reactions at each time point. Cross-linking is assessed by molecular weights of products, determined by electrophoresis under reducing conditions on 10% SDS polyacrylamide gel. Particularly, cross-linking is assessed by formation of gamma chain dimers and, at later time points, loss of gamma chain monomers (as described in Lorand, *Ann. N.Y. Acad. Sci.* 202(6) (1972). The results of these cross-linking assays show that transgenic saliva-derived fibrinogen has substantially the same cross-linking kinetics as fibrinogen from human plasma, except that the plasma samples show a small amount of dimerization even in the absence of Factor IIIa, (due to residual plasma Factor XIIIa), and slight molecular weight heterogeneity not seen in the saliva samples (due to naturally occurring gamma chain variations that do not occur in the transgenic fibrinogen).

(17) Germ Line Transmission

Transgenic cows that produce high levels of the transgenic product in their saliva are interbred. The offspring are evaluated for transmission of the transgenic DNA and for expression of the transgene product saliva, as described above. Of 4 cows that produce high levels of the transgenic product in saliva, 2 transmit the transgene to offspring.

The following claims are illustrative of the subject matter of the invention sought to be patented:

1. A transgenic bovine whose genome comprises a nucleic acid encoding at least one transgenic polypeptide, comprising a secretion signal, said nucleic acid operably linked to a salivary gland-specific cis-acting 5' transcription control region, wherein said control region comprises a bovine salivary gland protein promoter selected from the group consisting of bSP30a and bSP30b, wherein said polypeptide is expressed and secreted in the saliva of said transgenic bovine.

2. The bovine of claim 1, wherein said polypeptide is an active form.

3. The bovine of claim 1, wherein said polypeptide is a proactive form.

4. The bovine of claim 1, wherein said transgenic polypeptide is human.

5. The bovine of claim 1, wherein said transgenic polypeptide is produced at a level ranging between approximately 0.5 mg/ml-5.0 mg/ml.

6. The bovine of claim 4, wherein said human transgenic polypeptide is selected from the group consisting of phytase, an antibody, a growth hormone, a blood protein, serum albumin, fibrinogen, prothrombin, thrombin and von Willebrand Factor ("vWF").

7. The bovine of claim 1, wherein said transgenic polypeptide has the activity of the naturally occurring polypeptide.

8. The bovine of claim 1, wherein the activity of said transgenic polypeptide is from 25% to 95% of the activity of the naturally occurring peptide.

9. The bovine of claim 3, wherein said proactive form is converted into said active form.

10. The bovine of claim 1, further comprising a flexible tubing inserted into at least one salivary gland duct pair, wherein said pair comprises a first and second salivary gland.

11. The bovine of claim 10, wherein said salivary gland pair comprises a parotid gland pair.

12. The bovine of claim 1, wherein said transgenic polypeptide is selected from the group consisting of phytase, an antibody, a growth hormone, a blood protein, serum albumin, fibrinogen, prothrombin, thrombin and von Willebrand Factor ("vWF").

13. A method, comprising:
a) providing;
   i) a transgenic bovine whose genome comprises a nucleic acid encoding at least one transgenic polypeptide, said nucleic acid operably linked to a salivary gland-specific cis-acting 5' transcriptional control region, wherein said control region comprises a bovine salivary gland protein promoter selected from the group consisting of bSP30a and bSP30b, said bovine producing saliva, wherein said polypeptide is produced in said saliva;
   i) a flexible tubing to collect said saliva;
b) making a surgical incision in said salivary gland duct;
c) cannulating said duct with said tubing; and
d) collecting said saliva.

14. The method of claim 13, wherein said collecting comprises a collection device.

15. The method of claim 13, further comprising the step of isolating said polypeptide from said saliva.

16. The method of claim 13, wherein said transgenic polypeptide is human.

17. The method of claim 16, wherein said human transgenic polypeptide is selected from the group consisting of phytase, an antibody, a growth hormone, a blood protein, serum albumin, fibrinogen, prothrombin, thrombin and von Willebrand Factor ("vWF").

18. A method, comprising:
a) providing;
   i) a first DNA sequence comprising 5' cis-acting expression signals, said first DNA sequence being derived from a first salivary gland secretory protein gene, said first gene comprising a bovine salivary gland protein promoter selected from the group consisting of bSP30a and bSP30b;
   ii) a second DNA sequence encoding a polypeptide of interest and a region encoding an operable secretion signal, said secretion signal being derived from a second salivary gland secretory protein gene; and
   iii) a third DNA sequence comprising termination and 3' regulatory signals, said third DNA sequence being derived from a third salivary gland secretory protein gene, wherein said first, second, and third salivary gland secretory protein genes are not necessarily different;
b) joining said first, second, third DNA sequences in operable linkage effective for salivary gland expression and saliva-specific expression of said polypeptide of interest to create a transgene construct;
c) cloning said transgene construct to produce a vector;
d) microinjecting said vector into a bovine zygote; and
e) transferring said bovine zygote produced in step (d) into a psudeopregnant female of the same species, thereby producing a transgenic bovine whose genome comprises a transgenic polypeptide transgene which results in expression and secretion of said polypeptide in saliva of said bovine.

19. The method of claim 18, wherein said transgenic polypeptide is human.

20. The method of claim 19, wherein said human transgenic polypeptide is selected from the group consisting of phytase, an antibody, a growth hormone, a blood protein, serum albumin, fibrinogen, prothrombin, thrombin and von Willebrand Factor ("vWF").

* * * * *